(12) United States Patent
Thorne, Jr. et al.

(10) Patent No.: US 7,048,720 B1
(45) Date of Patent: May 23, 2006

(54) MULTI-CHAMBER, SEQUENTIAL DOSE DISPENSING SYRINGE

(75) Inventors: Gale H. Thorne, Jr., Bountiful, UT (US); Nestor Rodriguez San Juan, Eaton, PA (US); Michael Wallace Howlett, Salt Lake City, UT (US); Bradley Carling Robinson, North Salt Lake, UT (US); Gale H. Thorne, Bountiful, UT (US)

(73) Assignee: Infusive Technologies, LLC, Bountiful, UT (US)

( * ) Notice: Subject to any disclaimer, the term of this patent is extended or adjusted under 35 U.S.C. 154(b) by 0 days.

(21) Appl. No.: 11/284,504

(22) Filed: Nov. 22, 2005

Related U.S. Application Data

(63) Continuation-in-part of application No. 10/838,101, filed as application No. PCT/US05/14299 on Apr. 26, 2005, now Pat. No. 6,997,910.

(51) Int. Cl.
*A61M 5/00* (2006.01)
*A61M 5/315* (2006.01)

(52) U.S. Cl. ...................... 604/191; 604/231

(58) Field of Classification Search ............... 604/191, 604/218, 89–91, 184, 213, 226, 231, 237, 604/238, 523, 609
See application file for complete search history.

(56) References Cited

U.S. PATENT DOCUMENTS

| | | | |
|---|---|---|---|
| 3,976,068 A | 8/1976 | Lundquist | |
| 4,643,721 A * | 2/1987 | Brunet | ........................ 604/191 |
| 4,668,223 A | 5/1987 | Grotenhuis | |
| 4,792,329 A | 12/1988 | Schreuder | |
| 4,929,230 A | 5/1990 | Pfleger et al. | |
| 5,171,220 A | 12/1992 | Morimoto | |
| 5,213,236 A | 5/1993 | Brown et al. | |
| 5,236,420 A | 8/1993 | Pfleger et al. | |
| 5,271,531 A | 12/1993 | Rohr et al. | |
| 5,298,024 A * | 3/1994 | Richmond | ................... 604/90 |
| 5,695,465 A | 12/1997 | Zhu | |

(Continued)

OTHER PUBLICATIONS

"Debioject (ClipnJect)" from www.debiotech.com, pp. 1-3.*

(Continued)

*Primary Examiner*—Sharon Kennedy
(74) *Attorney, Agent, or Firm*—Gale H. Thorne

(57) ABSTRACT

A valve assembly is disclosed which partitions a conventional syringe into proximal and distal chambers to provide a multi-chamber, sequentially dispensing syringe apparatus. Incorporated in the valve assembly is a valved stopper having a valve (e.g. a slit valve) and a separator which filters out gas from liquid being dispensed through the valve assembly. A syringe plunger communicates through fluid in the proximal chamber to force displacement of the valve assembly. The valve is actuated by differential pressure of a force greater than the valve assembly displacement force. The valve assembly may be made from two parts: (1) a valved stopper (may be molded from basic syringe plunger material); (2) a separator (may be injection molded from syringe barrel material). Key features of such a multi-chamber syringe apparatus are (1) fluids in the chambers are kept disparate; (2) the valve assembly may be used in conventional syringes; (3) gas in a closed chamber is filtered from delivered liquid; (4) bi-stable operation of a valve assembly valve permits reflux free operation; (5) a clinch in the separator holds the valve securely closed until the valve is opened by a predetermined action, such action being tactilely sensible. A tubing set is disclosed which may be added to provide a third disparate chamber.

52 Claims, 17 Drawing Sheets

U.S. PATENT DOCUMENTS

| | | | |
|---|---|---|---|
| 5,704,520 A | 1/1998 | Gross | |
| 5,704,918 A * | 1/1998 | Higashikawa | 604/191 |
| 5,713,857 A | 2/1998 | Gremard et al. | |
| 5,743,886 A | 4/1998 | Lynn et al. | |
| 5,743,890 A | 4/1998 | Hjertman | |
| 5,785,682 A * | 7/1998 | Grabenkort | 604/82 |
| 5,830,193 A | 11/1998 | Higashikawa et al. | |
| 5,851,200 A | 12/1998 | Higashikawa et al. | |
| 5,899,881 A | 5/1999 | Grimard et al. | |
| 6,027,481 A | 2/2000 | Barrelle et al. | |
| 6,045,004 A | 4/2000 | Elliott | |
| 6,077,252 A | 6/2000 | Siegel | |
| 6,120,478 A | 9/2000 | Moore et al. | |
| 6,132,400 A | 10/2000 | Waldenburg | |
| 6,142,977 A | 11/2000 | Kolberg et al. | |
| 6,149,628 A * | 11/2000 | Szapiro et al. | 604/191 |
| 6,161,364 A | 12/2000 | Kolberg | |
| H2027 H | 6/2002 | Brown et al. | |
| 6,544,233 B1 | 4/2003 | Fukui et al. | |
| 6,602,223 B1 | 8/2003 | Szapiro et al. | |
| 6,622,721 B1 | 9/2003 | Vedrine et al. | |
| 6,641,561 B1 | 11/2003 | Hill et al. | |
| 6,723,074 B1 * | 4/2004 | Halseth | 604/201 |
| 6,740,062 B1 * | 5/2004 | Hjertman | 604/187 |
| 6,866,653 B1 * | 3/2005 | Bae | 604/191 |
| 7,001,362 B1 * | 2/2006 | Vincent | 604/191 |
| 2002/0192113 A1 * | 12/2002 | Uffenheimer et al. | 422/67 |

OTHER PUBLICATIONS

Debiotech brochure from internet address www.debiotech.com (accessed May 25, 2004).

* cited by examiner

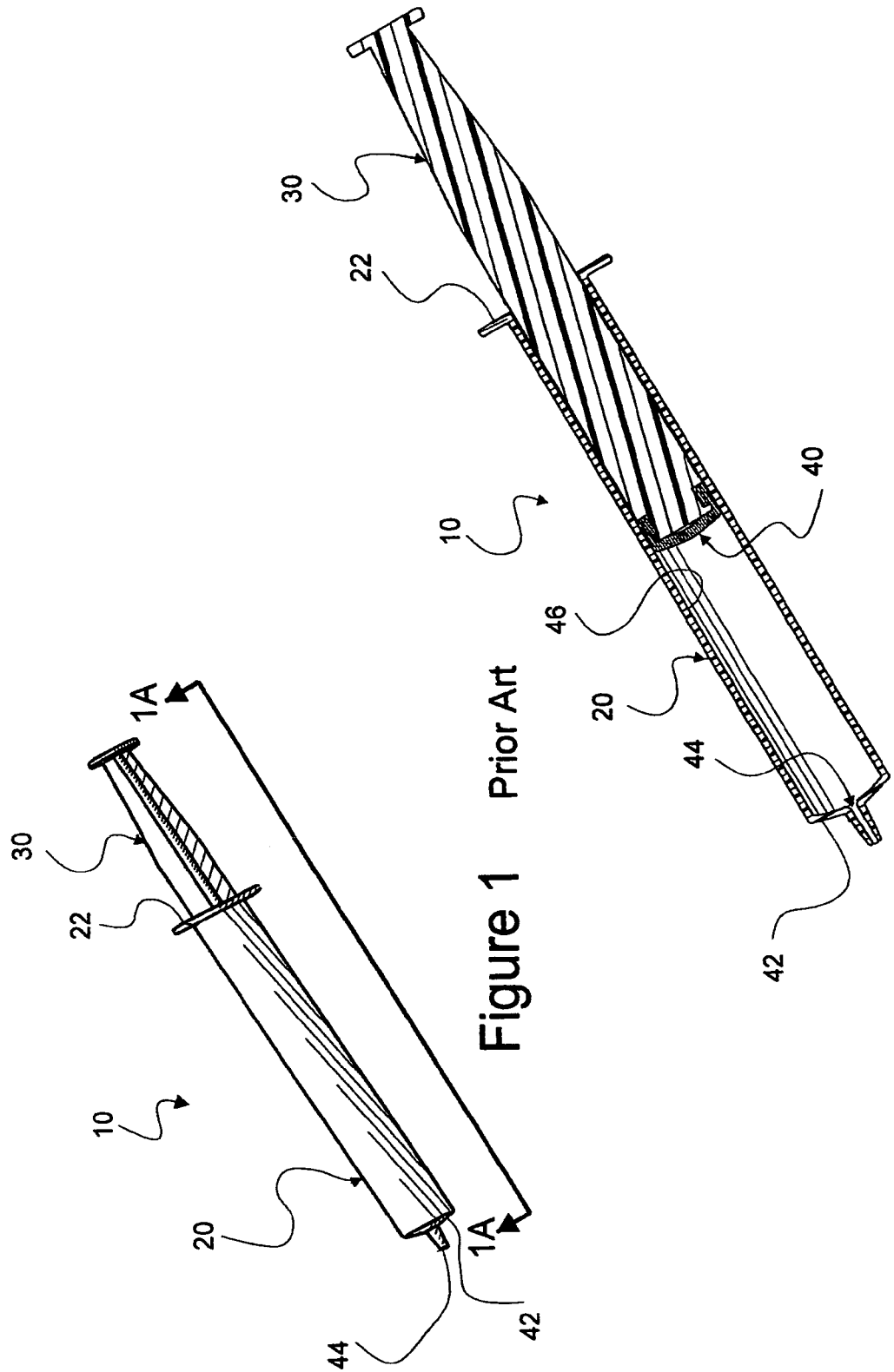

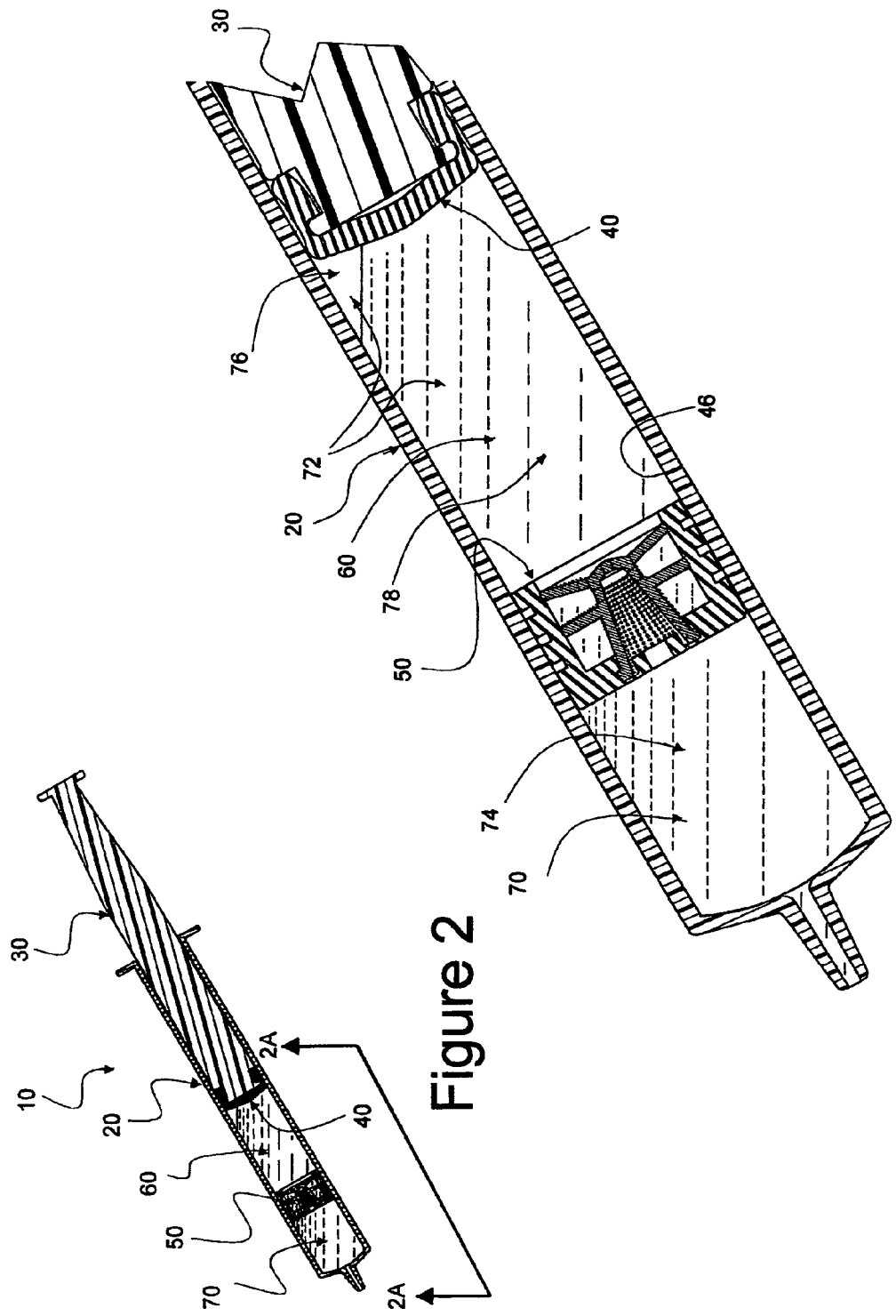

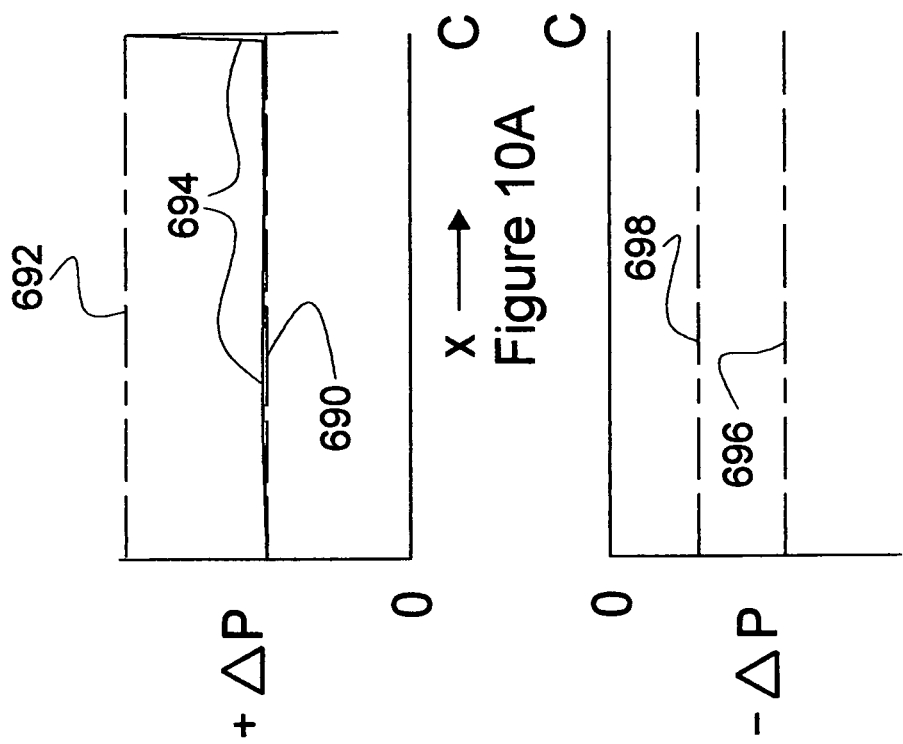
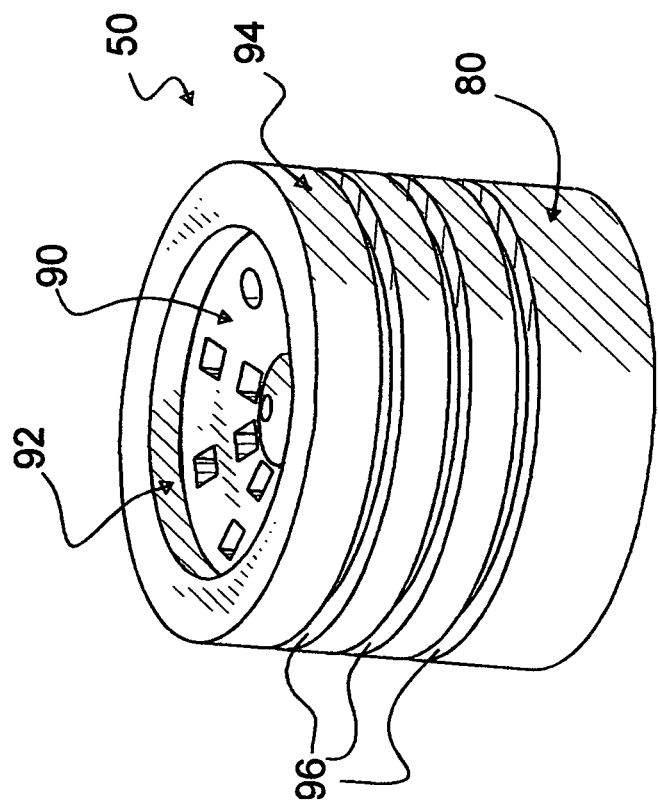

MULTI-CHAMBER, SEQUENTIAL DOSE DISPENSING SYRINGE

CONTINUATION-IN-PART

This patent application is a Continuation-in-Part of U.S. patent application Ser. No. 10/838,101 now U.S. Pat. No. 6,997,910 titled MULTI-CHAMBER, SEQUENTIAL DOSE DISPENSING SYRINGE, filed by Howlett, et al. on May 3, 2004 (Howlett) and issued on Feb. 14, 2006, which has an international PCT patent application number of PCT/US05/14299, filed Apr. 26, 2005.

FIELD OF INVENTION

This invention relates to multi-chamber syringes and, in particular, to syringes which dispense fluid from each chamber sequentially.

DESCRIPTION OF RELATED ART

During the last forty years, parenteral drug delivery has become increasingly common and sophisticated. It is currently estimated that nearly 90% of hospital patients receive IV medications, often through a variety of apparatus, including expensive electronic IV pumps and multi-channel infusion systems. Home care patients may receive antibiotics through an elastomeric "ball" pump. Syringe pumps are common in many hospital and alternate site settings and are often used as a low cost alternative to more expensive IV pumps.

Virtually all IV medications, administered through a catheter or IV tubing, must be flushed into the vascular system with saline or a similar physiologically compatible flushing fluid. Such flushing assures that a patient receives a full dose of medication, some of which otherwise might remain in the associated IV tubing or catheter. Flushing also assures that a subsequently infused incompatible medication does not come in contact with a previous one. It is well known in the infusion art that flush solutions are also used to keep an infusion line patent or open.

With rising healthcare costs, and an ever increasing shortage of nurses and pharmacists, there is a strong motivation to streamline basic procedures, such as IV catheter flushing to save clinician time. Noting that flushing usually necessitates use of a second flushing syringe (which is often currently factory pre-filled), the flushing syringe represents added cost, not only in clinician time, but in terms of required additional syringes. Use of multiple syringes also increases risk of medication error (incorrect selection of flushing liquid) and introduction of microorganisms (a function of number of IV line or catheter accesses).

As an example, it is currently estimated that there are over 500 million antibiotic and chemotherapy medications administered annually in the United States. Each of these administrations are taught to require a follow-on flush, currently necessitating use of a second syringe in most cases. Combining antibiotic or chemotherapy and flush medications in one multi-chamber, sequential dose syringe promises to save over 500 million syringes, yearly in the United States alone, plus that additional time required for two syringe delivery.

Multi-chamber syringes in various forms are well known. Commonly, multi-chamber syringes are offered for use as mixing syringes and for sequential delivery of disparate fluids, maintaining the fluids as disparate entities until delivered. Mixing syringes most often provide features for mixing contents of the chambers and for delivering the mixed fluids simultaneously. Though this invention may utilize a mixing syringe within one or more chambers, the invention, itself, is independent of methods of mixing which may be utilized in mixing syringes.

Generally, within each serial delivery syringe, chambers are separated by an intermediate sliding stopper which receives motive force communicated through an intermediate fluid from a primary stopper which is part of a plunger assembly against which an external force is applied. For disparate fluids to be dispensed sequentially or serially, each intermediate stopper must provide a fluid-tight seal until all fluid from a distal chamber is evacuated from the syringe. Once the distal chamber of the syringe is so purged, that intermediate stopper must be breached or bypassed to permit dispensing of the contents of a proximal or intermediate chamber.

An example of a multi-chamber syringe is provided in U.S. Pat. No. 4,929,230 titled SYRINGE CONSTRUCTION and issued May 29, 1990 to Frederick W. Pfleger (Pfleger). Pfleger teaches a distortable piston which is used as the intermediate stopper. The piston of Pfleger collapses upon contact with a distal end of a syringe to provide a fluid pathway to dispense contents from the intermediate chamber.

While a syringe made, as an example, according to Pfleger appears to provide a solution for sequentially dispensing disparate fluids, there are a series of concerns which would necessarily be associated with using such a syringe to dispense sequential doses of medications. A first concern arises, for example, when it is recognized that such a syringe may be used to dispense an accurately measured dose of a very expensive medication into an IV apparatus from a distal chamber of a multi-chamber syringe. Then, immediately following dispensing the first medication, a volume of a following solution is dispensed through the IV line to fully flush the first solution.

Clearly, a deformable piston, having a hollow portion, such as the stopper of Pfleger would not have zero dead space. Also, it is well known that filling procedures for contents of the proximal chamber may permit a quantity of air (or other gas) to be trapped therein. It may be noted that even if such gas is not trapped during filling, free gas may be found in the proximal chamber simply as a result of out-gassing. Pfleger does not teach a way of purging the proximal chamber of gas or of containing any gas in the proximal chamber while only dispensing liquid therefrom, making such a system unacceptable for use in directly administering intravenous liquid medications to a patient. While other art may provide more effective ways to deal with the dead space issue, there is no known art which teaches a way of delivering only liquid from the proximal or intermediate chambers. That such may be a problem is recognized by U.S. Pat. No. 5,236,420 titled BYPASS, PRESSURIZED PISTON FOR CHAMBERS issued Aug. 17, 1993, also to Frederick W. Pfleger, discloses a valved plunger which may be used to evacuate gas from a proximal syringe chamber.

Other art, such as U.S. Pat. No. 6,027,481 issued Feb. 22, 2000 to Laurent Barrelle, et al. (Barrelle) and U.S. Pat. No. 5,851,200 issued Dec. 22, 1998 to Tetsure Higashikawa, et al. (Hagashikawa) disclose multi-chamber syringes with sliding valves. However, in each case, Barrelle and Higashikawa teach special structure requirements imposed upon a syringe barrel (a channel in the case of Barrelle and a bulge in the case of Higashikawa) which is used to provide a fluid pathway about a stopper.

Another U.S. patent, numbered U.S. Pat. No. 6,723,074 B1, titled SEQUENTIAL DELIVERY SYRINGE and issued Apr. 20, 2004 to Thor R. Halseth (Halseth) teaches a sequential delivery syringe which utilizes a modification to a discharge opening of a syringe for providing access to a rear chamber of a two chamber syringe. The modification comprises disposing a piercing member at the discharge opening. The piercing member punctures a "mid-piston" and a collapsible bag disposed in a rear chamber to provide access to fluid in the bag. Access occurs when the mid-piston is displaced by action of a plunger and stopper piston to cause the mid-piston and bag to contact the piercing member.

Definition of Terms:

Following is a brief list of clarifying definitions for terms used in this Application:

assembly n: a device which is made from at least two interconnected parts barrel n: a cylindrical elongated portion of a syringe which is conventionally open on one end to receive a plunger and stem used for displacing fluid within the barrel and partially closed at an opposite end except for an orifice through which fluid is ejected or aspirated bi-stable adj: a descriptor for a device having two stable states clinch n: a structure or device which acts upon a part to clamp it closed while in contact therewith conventional adj: a sanctioned by general custom; i.e. commonplace, ordinary chamber n: a volumetric portion of a divided barrel disparate n: when used in conjunction with a liquid volume, a volume of liquid which is distinctly separate from another liquid volume differential pressure ($\Delta P$) n: a pressure gradient resulting from unequal pressures exerted upon opposing sides of a structure; generally as used herein, $\Delta P = P_p - P_d$ distal adj: a term which depicts placement away from a reference point (e.g. away from a user of a syringe)

dome n: an arcuately shaped surface (e.g. a hemisphere)

downstream adj: a direction which is consistent with flow out of a syringe or away from a user fluid n: a substance (e.g. a liquid or gas) which tends to take the shape of a container front adj/n: distally disposed or a distally disposed site (e.g. a front of a syringe comprises the barrel orifice)

gas n: a fluid which is neither solid nor liquid gas separator n: a liquid filter which inhibits gas flowing there through liquid n: a fluid which is neither solid nor gaseous, free flowing like water non-planar adj: not planar in a resting or stable state medial adj: occurring away from an outer edge; disposed near the center of (e.g. disposed away from an edge or periphery and in the vicinity of a center of gravity or axis of symmetry)

$P_d$ n: pressure in a distal chamber plunger n: a portion of a syringe piston apparatus usually affixed to a syringe stem which is used to displace fluid within a syringe barrel prime v: to fill liquid into a cavity generally by removing air therefrom (e.g. priming a gas separator)

$P_p$ n: pressure in a proximal chamber proximal adj: opposite of distal (e.g. a term which depicts placement nearer than a reference point)

rear adj: opposite from front (i.e. generally associated with a part of a syringe barrel which is proximal to a syringe user)

reflux n: a type of undesired retrograde (upstream) flow of liquid (e.g. blood) into a catheter or the like from a vessel in which the catheter or the like resides separator n: a liquid filter which impedes passage of air as liquid flows through the separator stiction n: a special case of friction; stiction being the force required to initiate motion to a resting body, esp. when stiction is greater than moving friction stem n: an elongated part which fits within a syringe barrel and is affixed to a plunger for the purpose of displacing fluid within the barrel stop n: a obstruction which is differentiated from friction or stiction which halts displacement of a stopper or plunger stopper n: a plunger associated with a stopper assembly, in the instant invention, the stopper contains a self-actuating bi-stable valve syringe n: a device used for injecting or withdrawing fluids upstream adj: a direction which is against the direction of flow from a syringe (opposite of downstream)

BRIEF SUMMARY AND OBJECTS OF THE INVENTION

In brief summary, the currently preferred embodiment of this novel invention alleviates all known problems related to providing an effective multi-chamber, sequential dose dispensing syringe. Inherently, the invention involves a stopper assembly which is disposed to operate within a conventional, substantially constant diameter syringe barrel to separate a distal chamber from a proximal chamber. Before dispensing, the distal chamber generally contains a first volume of liquid. The proximal chamber contains a disparate second volume of fluid. A closed valve in the stopper assembly keeps the contents of each chamber separate from the other.

In this currently preferred embodiment, the stopper assembly comprises two elements, a valved stopper and a stopper stabilizer and gas separator (referenced hereafter as a "separator"). The valved stopper contains a valve mechanism which is only actuated to open after the stopper is displaced to collide with an associated distal end of the syringe (or another stop within the syringe) in which the stopper assembly is disposed. This embodiment, though novel on its own, is related to the invention disclosed in Howlett, the U.S. patent application from which this Application continues-in-part, disclosure and teaching of which are contained herein by reference.

In all embodiments of Howlett and this instant invention, action upon a plunger associated with the syringe communicates through the second volume of fluid to displace a stopper assembly to the syringe end, open the valve thereby dispensing liquid from the distal chamber. Upon complete evacuation of the liquid from the distal chamber and by collision of the stopper assembly with the distal internal end surface of the syringe (or another stop), a positive differential pressure across the stopper assembly resulting from force against the syringe stem causes the valve to be opened. Thus, continuous action upon the stem of the syringe permits sequential and selective dispensing of liquid contents from the proximal chamber following dispensing of fluid from the distal chamber.

In a preferred embodiment of this invention, the valve assembly comprises a bi-stable valve structure, the valve itself being characterized as a slit valve. It should be noted that a stopper assembly according to this instant invention operates in an unmodified standard or conventional syringe barrel, requiring no unconventional barrel features. Examples of some previously cited special features which may be placed in modified syringe barrels are found in Barelle and Hagashikawa. Note that bi-stable action of the valve provides for syringe operation only after valve opening which mimics in all ways operation of a conventional syringe. Also, with the valve remaining in an open state after pressure is removed from the proximal chamber, any residual pressure associated with stored energy within the proximal chamber acts against reflexive flow to thereby oppose reflux in an attached catheter or other dispensing tube.

Selective opening of the valve is based upon a common geometry of most, currently commercially available conventional syringe barrels. All such syringe barrels have a substantially constant diameter hollow barrel abruptly closed at a distally disposed inner surface. Distally, the inner surface commonly comprises a centrally disposed orifice through which fluid is dispensed from the barrel. Generally, a plunger, with an associated stopper affixed thereto, is provided for forced displacement of fluid through the barrel and orifice.

To prevent premature mixing of the disparate solutions in syringe chambers, the stopper assembly valve must open only upon being displaced to its most distal site in contact with the distal end of the syringe barrel (a stop). For this reason, the stopper assembly comprises a structure which is affected by collision between a surface at that distal site (the stop) and, then, reacts to open the valve when additional pressure is forced upon the valve. In addition, to assure that the valve remains absolutely closed until fluid is dispensed from the distal chamber, the separator is preferably disposed and structured to act as a clinch, applying a closing, supporting force upon the valve until the valve is displaced from the clinch by a downstream-directed positive differential force across the valve.

To assure effective clinching support by the separator prior to opening the valve, the separator must be securely connected to the valved stopper and be displaced as the valved stopper is displaced. As is well understood in fluid mechanics, displacement of a substantially incompressible fluid in a proximal chamber of a syringe barrel interposed between a combination of a proximally disposed syringe stem and associated plunger and a distally disposed valve assembly, results in like displacement of the valve assembly as the stem and associated plunger are displaced. The valved stopper and separator of the instant invention, therefore, comprise an interlocking interface which causes the separator to be securely affixed to the valved stopper and to be jointly displaced as the stem stopper is displaced.

An important feature of a multi-chamber syringe is a provision for only dispensing flow from any proximally disposed chamber (relative an initial distal chamber) to guard against reflux (retrograde flow) into a catheter or tube upon completion of a given dispensing cycle or operation. For this reason, a valve assembly should operate to impede retraction of fluid at the end of such dispensing or at completion of a dispensing operation. When no interlock is available from an external associated part, such as from the separator, a valve disposed within the valved stopper must be self actuating and, once open must either close without drawing fluid back into the syringe or remain open to assure that no reflux occurs. Therefore, it is preferred that a valve disposed in the stopper assembly be bi-stable. (i.e. the valve must be stable in the closed state until forced open and be disposed to remain in a stable open state, once opened.)

In a preferred construction, such a valve is non-planar (e.g. the valve structure may be dome shaped). In the case of a dome-shaped valve, care must be taken to assure that displacement of the valve upon switching does not collide with the front inner surface of the associated syringe to thereby make switching and opening of the valve difficult.

Non-planar or dome valves are well known, especially for self closing food containers. As an example, U.S. Pat. No. 5,213,236 issued May 25, 1993 to Paul E. Brown, et al. (Brown), discloses a slit valve having a rotating hinge. However, Brown discloses a slit valve which is opened by pressure applied to an associated container and which is self closing when pressure is taken from the container. By repetition, it is emphasized that, for two very important reasons, a valve according to the instant invention should not so close after being opened. First, such closure would most likely cause fluid to be withdrawn from an output flow path and, second, force of closing would act against force being used to drive liquid from the proximal chamber, making purging of the proximal chamber more difficult than if the valve were bi-stable and remains in an open state.

Of course, the slit valve must only open when the valve assembly collides with the distal inner surface of the associated syringe or stop. In all other cases, until so opened, the valve must remain securely closed. As a syringe operation may require bi-directional displacement of a syringe stem and resulting bi-directional displacement of the valve assembly, it is important to construct the valved stopper and separator to properly provide closure support, if needed, by the slit valve in all such modes of displacement. For this reason, the separator, which is securely affixed to the valved stopper and thereat disposed about the valve slit as a clinch, preferably comprises a set of ribs which cooperate to provide clinching support for the valve about the slit. Thus restrained, the slit valve does not open inappropriately, especially when the syringe stem is proximally displaced.

As noted in the patent application from which this application is a continuation-in-part, when pre-filled doses are stored in the proximal chamber for ultimate use, it is not uncommon for gas (most commonly air) to collect in a non-insignificant bubble size there inside. It is not good medical practice to dispense that gas into a patient line (e.g. an IV line). To preclude such an occurrence, the valve assembly comprises a liquid filter which is interposed across fluid flow through the valve to act as a gas separator. The gas separator is formed in a centrally disposed portion of a a separator body which may be made as a hollow frustoconical shape, being open at the bottom. A series of small, closely spaced holes are dispersed about the conical sides of the separator body. The top (proximal face) of the frustoconical or thimble shaped body is closed except for at least one hole which provides a sufficiently large exit to permit purging of gas from the separator and delivery of at least part of the liquid from the proximal chamber therethrough. The bottom of the separator is open and disposed distally toward the valved stopper to contact the inner surface of the stopper about the slit. An outwardly projecting rim about the bottom of the separator provides an interlocking surface for a complimentary groove molded into the valved stopper about the slit.

Also, stability of a freely displaced valve assembly within the barrel of a syringe must be considered. The body of the separator is provided with sufficient radially extending appendages to inhibit valved stopper canting.

The valve assembly may be made from only two parts. The valved stopper may be molded from flexible synthetic resinous material, consistent with material used in plunger stoppers. The separator may be injection molded from semi-rigid synthetic resinous material which is non-interactive with solutions stored in the proximal chamber. Such a material may be polypropylene and may be the same material used in an associated syringe barrel.

A critical factor in a valve assembly used in multi-chamber syringes is assembly cost. Such assembly should be uncomplicated and easily automated. For this reason, structure and function of the valved stopper and separator are sufficiently independent that the separator can be affixed to the valved stopper in any angular orientation relative to the plane of a slit in the valved stopper.

In an application for a multi-chamber syringe, a very toxic liquid (e.g. chemotherapy agents) may be stored in the distal chamber near the distal syringe orifice. To protect against inadvertent contact with such toxic liquid, it is preferred to provide some kind of a buffer. A novel addition to a multi-chamber syringe in the form of a tube set provides such a buffer. The tubing set comprises an elongated tube having a syringe connector (such as a luer fitting) on a proximal end and a gas separator assembly on the distal end. The tube is mostly filled with a buffer liquid, the liquid being separated from contents of the distal chamber of the syringe by a trapped air bubble. The gas separator assembly comprises a separator component to trap and filter out the air bubble and a fitting (such as a luer fitting) for connecting to downstream patient lines.

In summary, the valve assembly:

provides a selective partitioning between proximal and distal chambers of a multi-chamber syringe.

may be used in conventional (off the shelf) commercial syringes having constant diameter hollow barrels.

filters gas (e.g. air) from liquid delivered from the proximal chamber.

permits the distal chamber of the syringe to be used in the same manner as a conventional syringe prior to dispensing fluid from the proximal chamber.

in a preferred embodiment, provides a closed, bi-stable valve which is opened only after collision between the valve assembly and inner surface of the distal end of the syringe and which remains in an open state once opened.

has a valved stopper/separator interface which acts as a clinch to maintain a slit of the valved stopper closed until opened at the distal end of the syringe.

requires a tactilely sensible force to open the valve of the valved stopper after collision of the valve assembly with the distal end of a syringe.

does not displace fluid proximally at an end of a proximal chamber dispensing cycle, thereby permitting the device to operate reflux free.

separates gas from liquid and only dispenses liquid from the proximal chamber.

comprises parts which stabilize the valve assembly throughout displacement.

permits the valve to open only upon contact with a distal end of a syringe or other stop within the barrel of the syringe Accordingly, it is a primary object to provide a valve assembly which partitions a conventional commercial syringe to make a multi-chamber syringe.

It is a fundamental object to provide a valve assembly for a syringe which keeps two disparate fluids apart until one of the fluids has been dispensed from the syringe.

It is an important object to provide a valve assembly which has a low dead space for liquid dispensed from a distal chamber.

It is another important object to provide a valve assembly having an operable slit valve.

It is yet another object to provide a valve actuator within a valved stopper which senses collision between a valve assembly and an inner surface at the end of a syringe (or other stop within the syringe barrel) and an increased pressure across the valved stopper to force a valving slit open.

It is a critical object to provide a bi-stable valve as part of the valved stopper.

It is another primary object to provide a valve assembly which opens to dispense liquid from a proximal chamber only after liquid from a distal chamber has been dispensed.

It is a basic object to provide a valve assembly which acts as a liquid filter in the proximal chamber to deter gas from being dispensed from the proximal chamber.

It is a very important object to provide a separator which is a stabilizer for an associated valved stopper in a syringe barrel.

It is an object to provide an interface between a valved stopper and a separator such that displacement of the valved stopper likewise displaces the separator.

It is an object to provide a multi-chamber syringe having a front chamber which may be used in the same manner as a conventional syringe prior to dispensing fluid from the proximal chamber.

It is a further object to provide a multi-chamber syringe combination which comprises the multi-chamber syringe disclosed supra plus an attached tubing set whereby three disparate liquids may be kept disparate and dispensed sequentially.

These and other objects and features of the present invention will be apparent from the detailed description taken with reference to accompanying drawings.

BRIEF DESCRIPTION OF THE DRAWINGS

FIG. 1 is a perspective of an exemplary commercial syringe with a plunger and stopper assembly disposed within the barrel of the syringe (prior art).

FIG. 1A is a section of the syringe seen in FIG. 1 taken along lines 1A—1A (prior art).

FIG. 2 is a section of a syringe, similar to the section seen in FIG. 1A, but with a valve assembly, as disclosed in Howlett, distally disposed relative to a plunger and stopper similar to the plunger and stopper of the syringe of FIG. 1.

FIG. 2A is a magnified portion, taken along lines 2A—2A, of the syringe seen in FIG. 2.

FIG. 3 is a perspective of the valve assembly seen in the syringe barrel in FIG. 2.

FIG. 10A is a graphical representation of critical operating pressures related to distal displacement and opening of a valve in a valve assembly.

FIG. 10B is a graphical representation of critical operating pressures related to proximal displacement and opening of a valve in a valve assembly.

DETAILED DESCRIPTION OF THE ILLUSTRATED EMBODIMENTS

Figure 4:
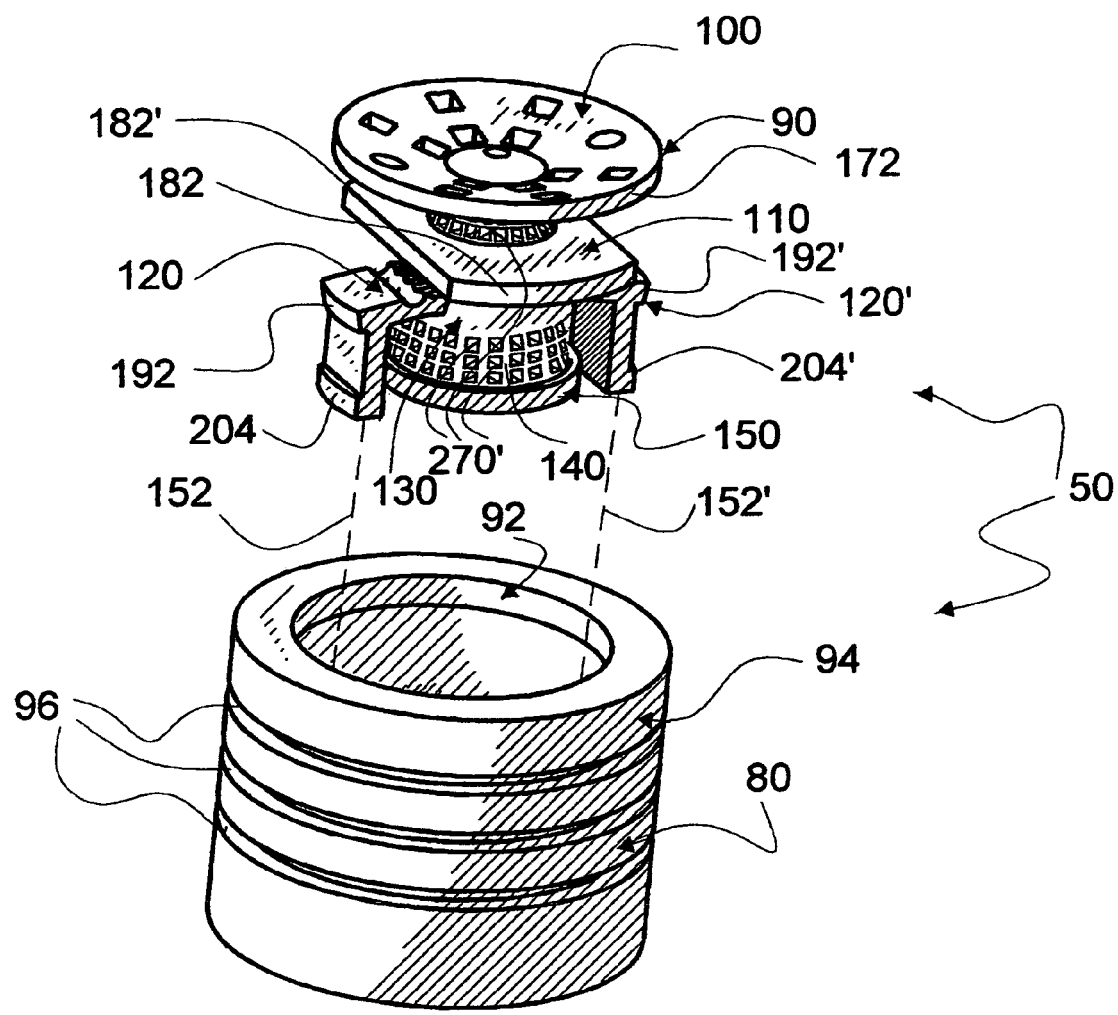
FIG. 4 is an exploded view of the valve assembly seen in FIG. 3 showing a valved stopper apart from a valve actuator.

In this description, primes of numbers are used to represent parts which are similar, but not identical to other parts having the same numbers. Reference is now made to embodiments illustrated in FIGS. 1–25 wherein like numerals are used to designate like parts throughout. It should be noted that FIGS. 1–6 are selected from figures disclosed in the U.S. patent application from which this application continues-in-part and are provided herein for ease of reference.

Prior art syringes (as exemplified by syringe 10) in FIGS. 1 and 1A, are available from a large number of commercial companies worldwide. Such syringes typically comprise an elongated hollow syringe barrel 20 which is open at a proximal end 22 to receive a syringe plunger 30 and stopper 40 and closed at a distal end 42 about a fluid transmission orifice 44. Generally, barrel 20 is of substantially constant diameter (within tolerances allowed by manufacturing methods, such as by injection molding for barrels made from synthetic resinous materials). Stopper 40 is compressible and sufficiently elastic when compressed to provide an efficient wiping action along the length of an internal cylindrical surface 46 of barrel 20.

As seen in FIG. 2, a valve assembly 50 (according to Howlett) is inserted into barrel 20 to divide space within barrel 20 into a proximal chamber 60 and a distal chamber 70. As seen in FIGS. 2 and 2A, each chamber, 60 and 70, may be filled with a volume of fluid, 72 and 74, respectively. It may be noted that, when chamber 60 is substantially filled with a volume of fluid (which should be mostly an incompressible liquid), displacement of stopper 40 results in substantially the same displacement of valve assembly 50. It may also be noted that fluid 72 disposed in chamber 60 is trapped and may contain a small bubble of gas, numbered 76, (which is likely air) associated with other liquid 78 also contained therein. Such gas 76 may be inadvertently trapped therein during filling or may be the result of outgassing or other gas producing phenomena following insertion of stopper 40 into barrel 20. In any event, such gas must be seriously considered and dealt with when such a device is used to dispense liquid to a patient to assure gas (air) is not injected into a patient line.

As disclosed in Howlett, a valve assembly 50, apart from a barrel 20, is seen in FIG. 3. Although more parts may be used in a valve assembly made according to the instant invention, valve assembly 50 comprises just two parts, a valved stopper 80 and a valve actuator 90. Note that valved stopper 80 has a hollow cylindrical well 92 into which valve actuator 90 is displaced for use.

Additional details of valved stopper 80 and valve actuator 90 are seen in FIG. 4. Valved stopper 80 has an outer cylindrical wall 94 which has a pattern of annular grooves, generally numbered 96, to facilitate sealingly wiping of inner surface 46 of barrel 20 as valve assembly 50 is displaced therealong (see FIG. 2A). Within well 92, valved stopper 80 comprises a plurality of grooves disposition and purpose of which are disclosed in detail in the original patent application from which this application continues-in-part.

As seen in FIG. 4, valve actuator 90 comprises a proximal stabilizing disk 100, a medially disposed stabilizing plate 110, a pair of actuator arms, 120 and 120', a medially disposed support body 130, into which is formed a gas separator vessel 140 and an annular connecting lip 150. Note vessel 140 is penetrated by a plurality of holes 270'. Valve actuator 90 is displaced into well 92 as indicated by dashed lines 152 and 152'.

Figure 5:
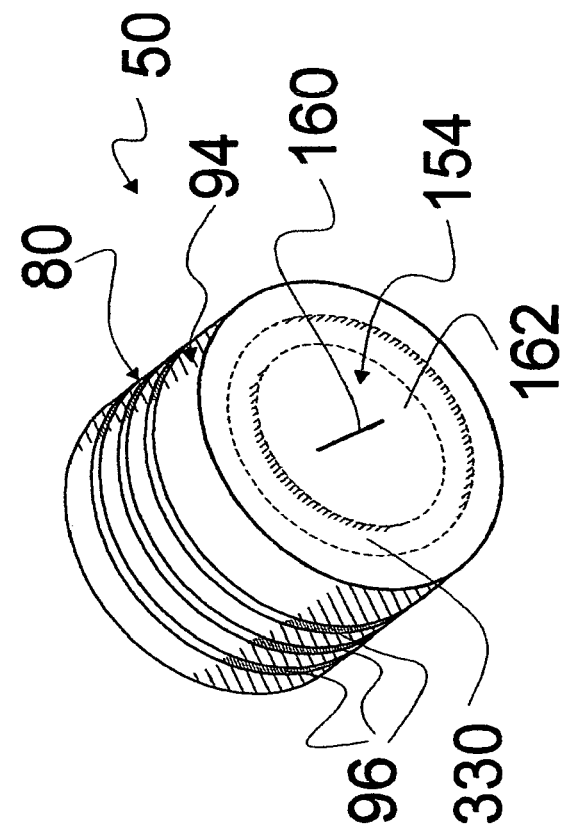
FIG. 5 is a perspective of the valved stopper, seen in FIG. 4, rotated such that the distal side of a slit valve is seen.

Distal end 154 of valve assembly 50 is seen in FIG. 5. Note, presence of a slit 160 which is medially disposed through a distal wall 162 of valved stopper 80. Slit 160 is formed as a closed valve which remains fluid tight until selectively opened by the action of arms 120 and 120' as disclosed in detail in Howlett. As arms 120 and 120' must be aligned with slit 160, special manufacturing methods, as also disclosed in Howlett, are required. Also note, a distal surface disposed annular ring 330 which raises that surface to collide with the inner surface of the distal end 42 of syringe 10.

Figure 6:
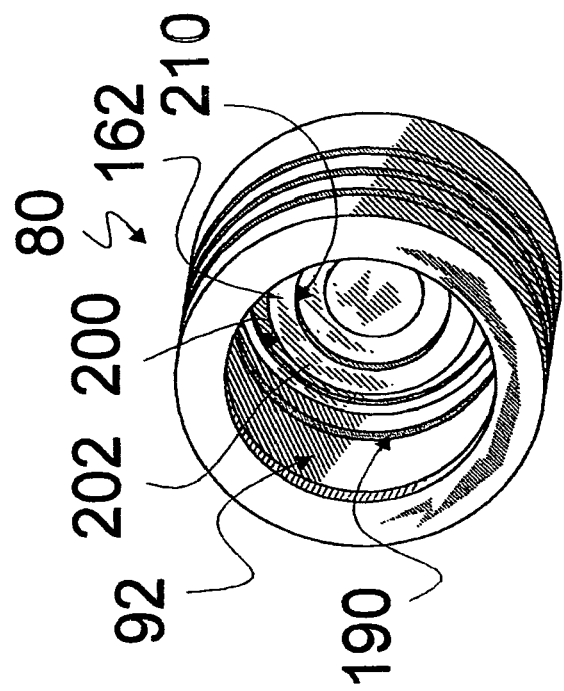
FIG. 6 is a perspective of a valved stopper, which is similar to the valved stopper seen in FIG. 5, but rotated such that the proximal side of the valve is seen.

Greater detail of construction of well 92 is seen in FIG. 6. Valved stopper 80 has a plurality of grooves and associated slots, each of which serve a specific purpose. However, there are no grooves for rim 172 of disk 100 and outer edges 182 and 182' of plate 110. (See FIG. 4.) Such grooves would impede distal displacement of valve actuator 90 within valve stopper 80. Such distal displacement is necessary for valve action, as is disclosed in detail in Howlett. A groove 190 (see FIG. 6) coincides with protrusions 192 and 192' of arms 120 and 120' (see FIG. 4), respectively. A slot 200, disposed on the inner side 202, of distal wall 162, coincides with extremities 204 and 204' of arms 120 and 120' (again see FIG. 4). Finally, an annular slotted groove 210 is also disposed on the inner side 202 of distal wall 162 to coincide with annular connecting lip 150, also seen in FIG. 4.

Of significant concern in valve assembly 50 is the requirement for a required alignment between slit 160 and arms 120 and 120'. Such an alignment requires special manufacturing methods as disclosed in Howlett and complex part handling during assembly of valve actuator 90 into valved stopper 80. As one skilled in molding and part assembly arts understands, there are a number of advantages of the presently preferred embodiment. For example, as is disclosed in detail hereafter, the part associated with gas separation of the currently preferred embodiment is more easily molded, the slit is more easily made, separate from other manufacturing procedures, in the valved stopper and the two parts are more easily assembled because there is no specific angular orientation of the gas separator relative to the slit.

Figure 7:
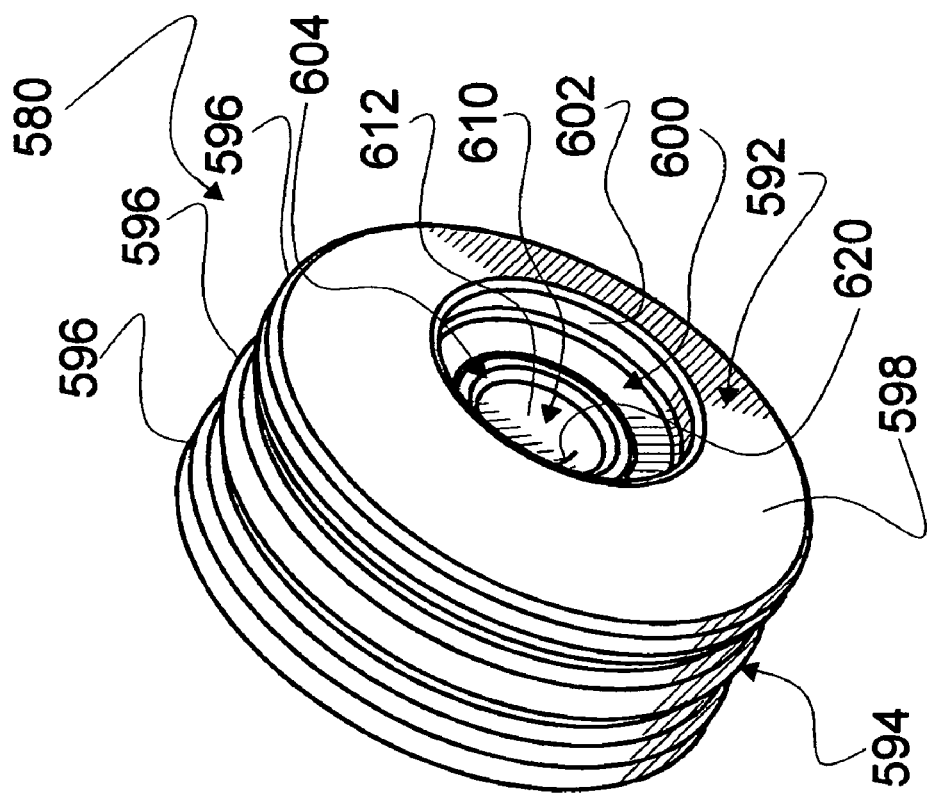
FIG. 7 is a perspective of a valved stopper of the currently preferred embodiment disposed to present a distal face of the valved stopper.
Figure 16:
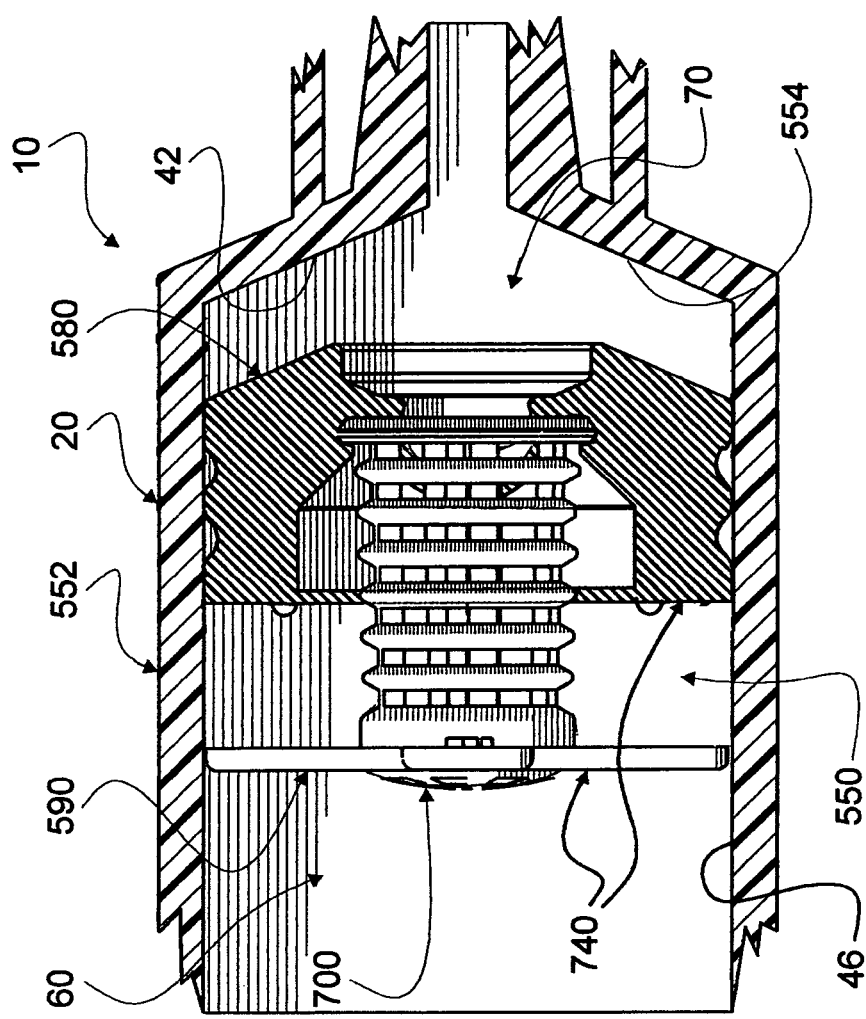
FIG. 16 is a side view of a portion of a syringe in which a valve assembly, constructed from the gas separator assembly seen in FIG. 15 and the valved stopper (in cross section) seen in FIG. 9, is disposed.
Figure 15:
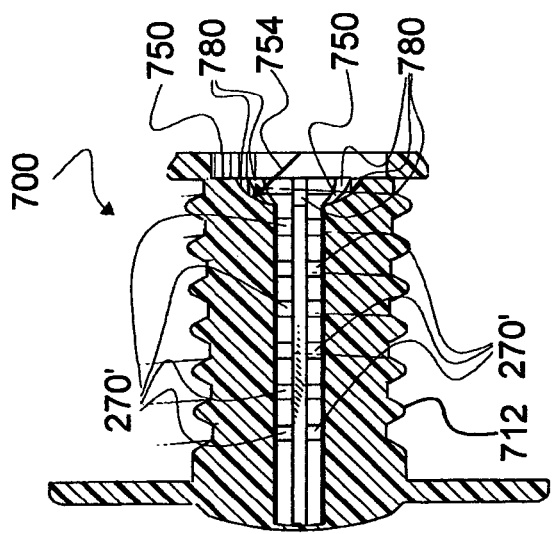
FIG. 15 is a section of the gas separator assembly seen in FIG. 13, the section being taken across two medially disposed ribs of the separator.

Reference is now made to FIGS. 7–25 wherein various details of the current preferred embodiment are seen. Initial reference is made to FIG. 16, where a valve assembly 550 is seen disposed within a portion 552 of a barrel 20 of a syringe 10. As seen in FIG. 16 syringe 10 ends in a surface or stop 554 having a predetermined concave or frustoconical shape 556 and a medially disposed orifice 44 through which fluid flows (see also FIGS. 1 and 2). Note that valve assembly 550 comprises a valved stopper 580 and a liquid filter or gas separator, generally referenced as separator 590. As seen in FIG. 7, valved stopper 580, comprises a distal surface 592 and an outer cylindrical wall 594. Wall 594 has a pattern of annular grooves, generally numbered 596, to facilitate sealingly wiping of inner surface 46 of barrel 20 as valve assembly 550 is displaced through barrel 20 (See FIG. 16.). Distal surface 592 comprises an outer facing ring 598 and a recessed medial portion 600. Outer facing ring 598 is preferably contoured to conform to an inner distal surface or stop 554 of distal end 42 of syringe 10.

Recessed medial portion 600 (see FIG. 7) is bounded by a cylindrical wall 602, an annular hinge 604, peripherally affixed to wall 602, and a medially disposed, non-planar valve 610 affixed to an inner portion of hinge 604. On a distal surface 612, a portion of a planar slit 620 is seen to be medially disposed in valve 610.

Figure 8:
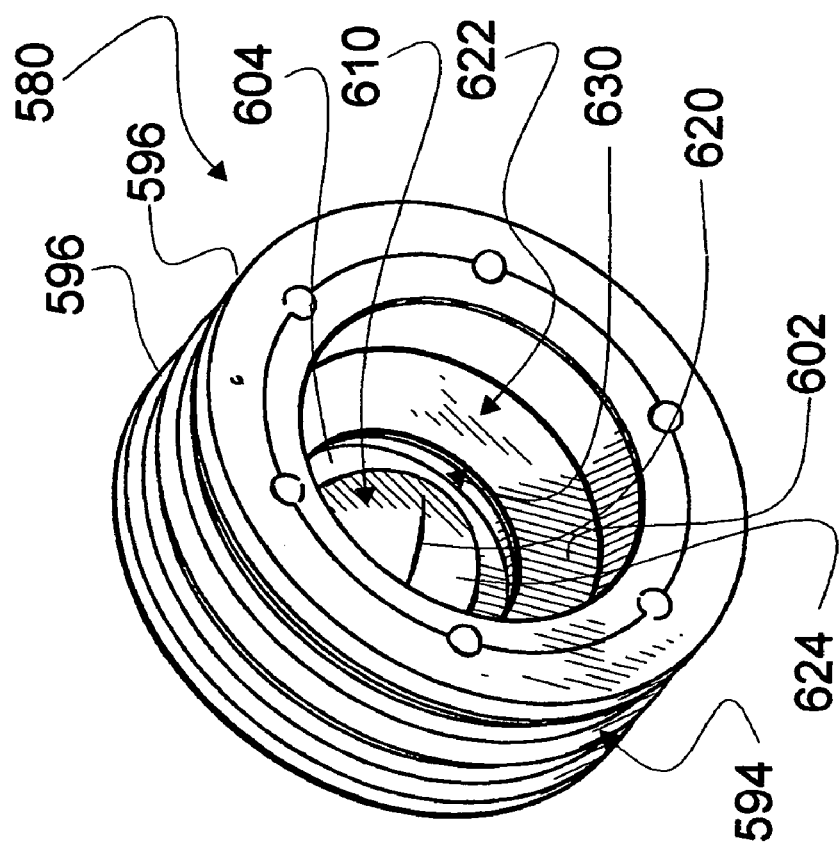
FIG. 8 is a perspective to the valved stopper seen in FIG. 7, the valve being rotated to present a proximal view.
Figure 9:
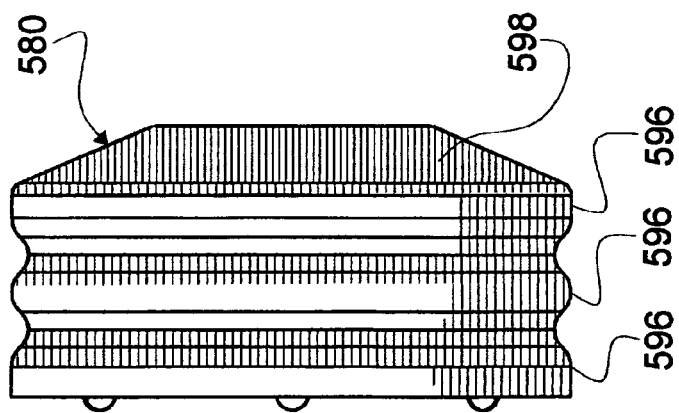
FIG. 9 is a side elevation of the valved stopper seen in FIGS. 7 and 8.
Figure 12:
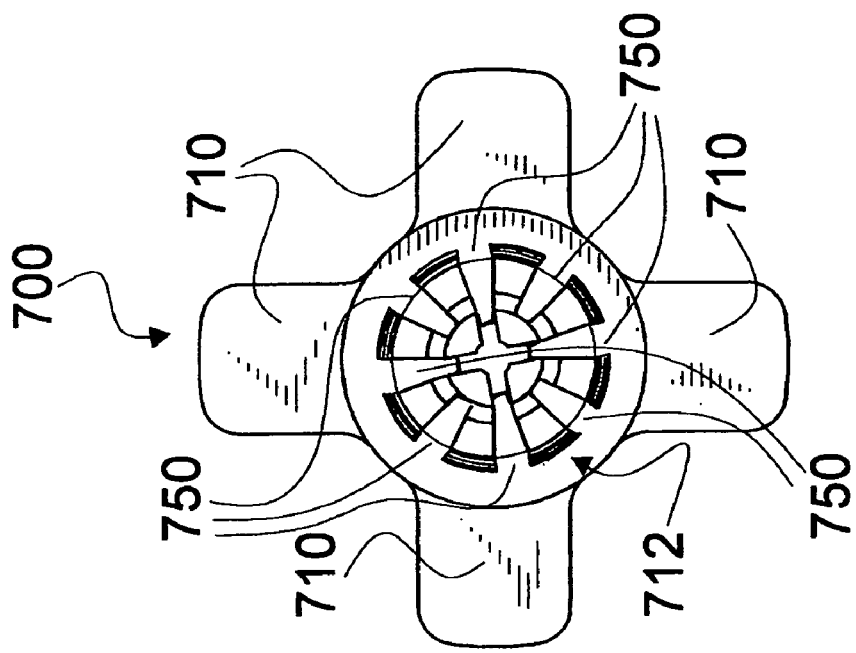
FIG. 12 is a rear elevation of the gas separator assembly seen in FIG. 11.

A Self-actuating Valved Stopper Valved stopper 580 is rotated in FIG. 8 to reveal a hollow cylindrical inner core 622, a distal interior surface 624 of valve 610, a portion of annular hinge 604 which circumscribes valve 610 and an annular groove 630, the purpose for which is disclosed in detail hereafter. Exterior shape and form of valved stopper 580 are seen in FIG. 9. Note frustoconical shape of surface 598, which is shaped to conform with contour of inner surface 554 of distal end 42 of syringe 10 to minimize dead space.

Figure 10:
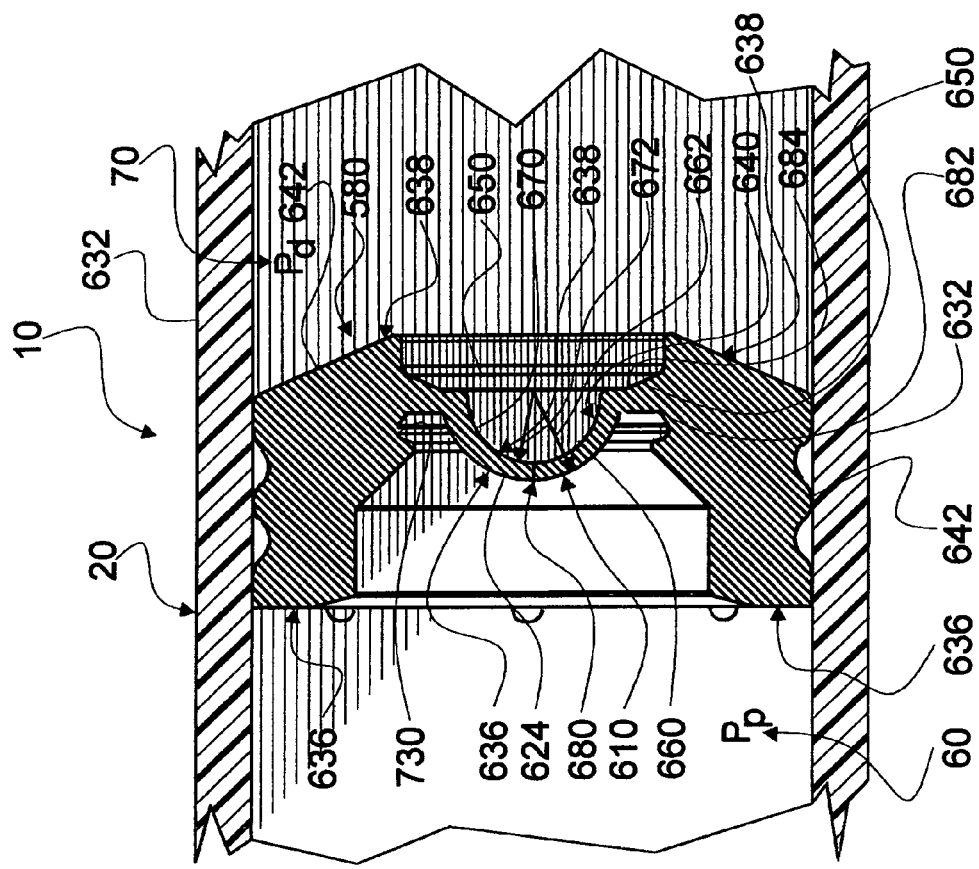
FIG. 10 is a cross-section of the valved stopper seen in FIG. 9.

A cross section of valved stopper 580 is seen in FIG. 10 to be disposed within a section 632 of a barrel 20. As such, valved stopper 580 divides space in barrel 20 into a proximal chamber 60 and a distal chamber 70. A pressure resident in chamber 60 is represented by $P_p$. A pressure resident in chamber 70 is represented by $P_d$. If $P_p$ is not equal to $P_d$, the non-zero pressure gradient is represented by $\Delta P$ (i.e. $\Delta P = P_p - P_d$). Note, that, if $\Delta P$ is positive, the resulting motive force upon proximally facing surfaces 636 of valved stopper urges valved stopper 580 toward end surface 554. If $\Delta P$ is negative, the resulting force upon distally facing surfaces 638 urges valved stopper 580 away from surface 554. Thus force upon plunger 30 of syringe 10 in a distal direction relative to barrel 20 tends to generate a positive $\Delta P$ and a force in a proximal direction relative to barrel tends to generate a negative $\Delta P$.

Due to the fact that stopper 580 is displaceable within barrel 20, $P_p$ and the associated $\Delta P$ is effectively limited when $\Delta P$ produces a force across surfaces 636 which overcomes friction (and stiction) to displace stopper 580. Note that, if a valve in Stopper 580 is also opened by a predetermined $\Delta P$, a force which overcomes friction to displace stopper 580 must be less than the force which results in opening a valve disposed in valve stopper 580.

As seen in FIG. 10, stopper 580 comprises a medially disposed, dome-shaped valve 640. Valve 640 is affixed to the remaining body 642 of stopper 580 via an annular hinge 650. It should be noted that, while valve 640 is hemispherical in shape, any valve shape which remains closed at a $\Delta P$ which displaces stopper 580 distally and which opens at a greater ΔP may be used within the scope of the invention. Such valves are usually non-planar. Further, as is disclosed in detail hereafter, there are important reasons for such a valve to remain open (be bi-stable) once being opened.

As may be noted in FIG. 10, valve 640 has a proximal surface 660 having a radius of curvature 662, a distal surface 670 having a radius of curvature 672 and a medially disposed slit 680. Hinge 650 has a thickened portion 682 where hinge 650 is affixed to remaining body 642 of stopper 580 and a thinned portion 684 where hinge 650 is affixed to valve 640. Thicknesses of hinge 650 and valve 640 determine ΔP necessary to open valve 640.

As an example, in a valve made to operate in a stopper for a 20 milliliter syringe, having an internal barrel diameter of approximately 0.8 inches, a valve assembly may be manufactured wherein the diameter of the stopper is increased to a diameter four percent grater than the internal barrel diameter. The proximal surface radius 662 may be approximately 0.25 inches. Thickness of the wall between surfaces 662 and 672 would be nominally 0.040 inches, although a variance of 0.012 may be allowed. Thickness of thickened portion 682 of annular hinge 650 was approximately 0.100 inches. Thickness of thinned portion 684 may be nominally 0.060 inches. Slit 680 is nominally approximately 0.160 inches.

Reference is now made to FIG. 10A which provides a graph o of a positive ΔP versus displacement of stopper 580 in a barrel 20. Zero (0) marks an initial stationary point of stopper 580 relative to a point of collision (C) between stopper 580 and surface or stop 554 (see FIG. 18). Dashed line 690 represents a pressure differential necessary to overcome friction (and stiction) to displace stopper 580. A second dashed line 692 represents a ΔP which forces valve 640 open. Solid line 694 is an example of ΔP as stopper 580 traverses through barrel 20. Note that ΔP 694 is substantially constant until collision between stopper 580 and surface 554 when ΔP 694 rises sharply to opening pressure differential 692, then falls rapidly as released flow decreases chamber 60 pressure. Note that any collision with a stop within barrel 20 would result in such a rise in ΔP.

Figure 18:
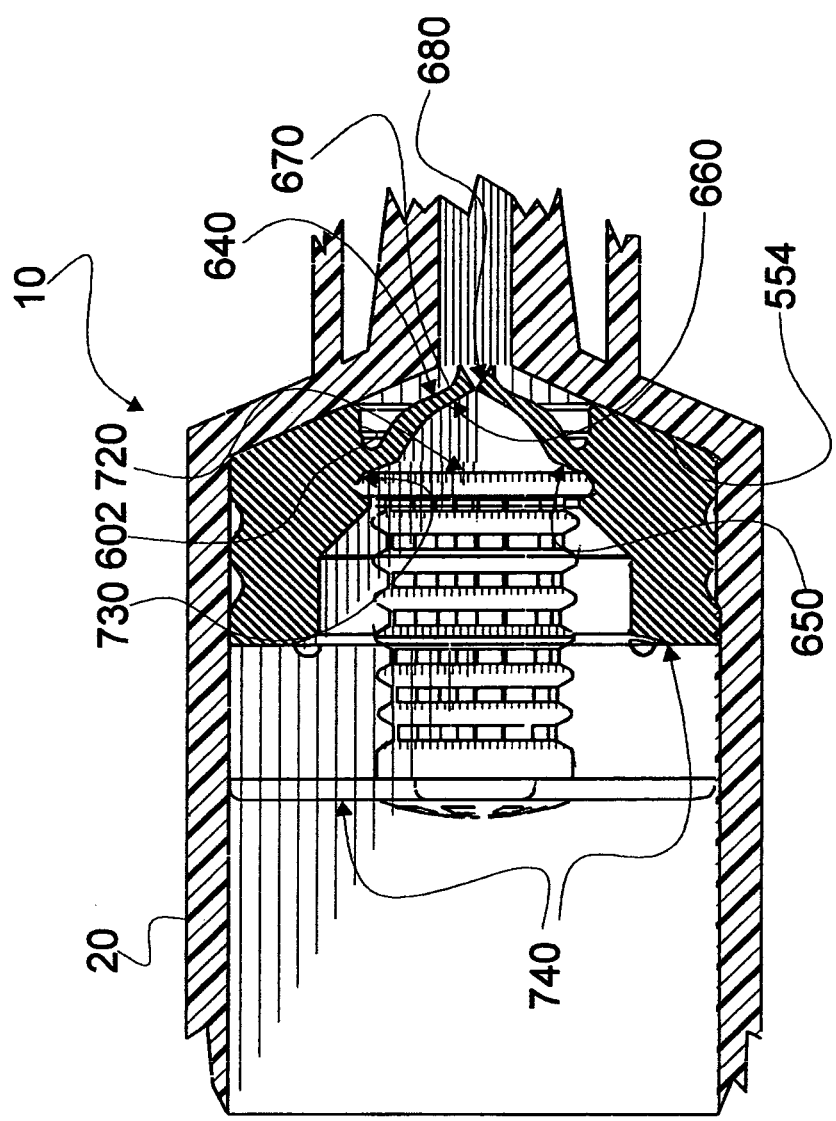
FIG. 18 is a side view of the portion of the syringe and valve assembly seen in FIG. 16, but with a valve portion of the valved stopper seen in a second bi-stable or open state.

An opened valve 640 is seen in FIG. 18. Note that, once valve 640 is forced to an open state, surfaces 660 and 670 are turned inside out (inverted). Surface 670, having the smaller radius of curvature of the two surfaces, tends to open slit 680 when dome-shaped valve 640 is inverted. The combination of inherent locking nature of the inverted surfaces and force imposed by annular hinge 650 tends to hold valve 640 in the open state providing a bi-stable valve which is maintained in an open state, once opened. Such a state has a definite advantage in IV therapy and is disclosed in detail hereafter.

An example of such a valved stopper has been made and tested by West Pharmaceutical Services, 101 Gordon Drive, PO Box 645, Lionville, Pa. 19341. As earlier disclosed, these valved stoppers were made with a diameter which is approximately four percent larger than an inner diameter of a 20 ml syringe barrel in which they were disposed. With such a design, pressure to slide a siliconized stopper was in the range of 2.4 to 5.6 pounds (generally about three to four pounds). Pressures to open the valved stoppers ranged from 12.50 to 22.2 pounds. While such pressure ranges may vary due to size and material factors, these pressures may be considered representative of pressure differentials evidenced in valve actuation. Material used in stoppers associated with these tests was West Formulation 4023/50 Gray.

A problem associated with a non-planar valve, when employing a syringe 10 to withdraw fluids into a front chamber 70 (as is done with a conventional syringe), is a tendency of the valve (e.g. dome-shaped valve 640) to "balloon" when ΔP is negative. Such ballooning tends to open slit 680 to open permitting cross-contamination of contents of chambers 60 and 70. As seen in FIG. 10B, a negative ΔP as indicated by dashed line 696 may be commonly disposed across valve 640 (as an example to fill chamber 70). Ballooning, opening an unclinched slit 680, may commonly occur at a smaller negative ΔP, indicated by dashed line 698. To solve this problem a restraint must be disposed about surface 660 in the form of a clinch to maintain slit 680 closed. For this and other purposes, a separator component (generally referenced separator 700) having a clinch, as seen in detail in FIGS. 11–15, is firmly affixed to stopper 580 about valve 640.

A Separator, Stabilizer and Clinch Separator 700 is similar to actuator 90 (see FIG. 4). However separator 700 is not required to comprise arms 120 and 120' because stopper valve 640 is self-actuating and is inherently bi-stable. A set of orthogonally disposed wings, generally numbered 710 (see FIGS. 13 and 14), are proximally disposed on a frustoconically shaped body 712 of separator 700 to provide stabilizing support when separator 700 is affixed to stopper 580 and disposed in a barrel 20. These wings 710 replace disk 100 and plate 110 of actuator 90 (see FIG. 4). Structure of holes, generally numbered 270' (see FIG. 15), is relatively unchanged from actuators disclosed in Howlett, except for a plurality of holes 270" disposed through a proximal face of separator 700 (see FIGS. 13 and 14). Holes 270' and 270" provide a low resistance pathway for liquid and a much higher resistance pathway for gas (air), thereby forming an effective liquid filter, filtering gas from dispensed liquid as do holes 270' of actuator 90.

On a distal side 714 of body 712 (see FIG. 11) separator 700 has an open throat 716. Disposed about throat 716 is a structure which forms an annular lip 720 (see FIG. 11). Referring once more to FIG. 10, stopper 580 is seen to have annular groove 730 disposed about dome valve 640. Lip 720 (see FIG. 11) and groove 730 comprise complementary shapes such that lip 720 fits into groove 730 to securely and sealingly affix separator 700 to stopper 640 to form a valve assembly 740 (see FIGS. 16–18).

Figure 11:
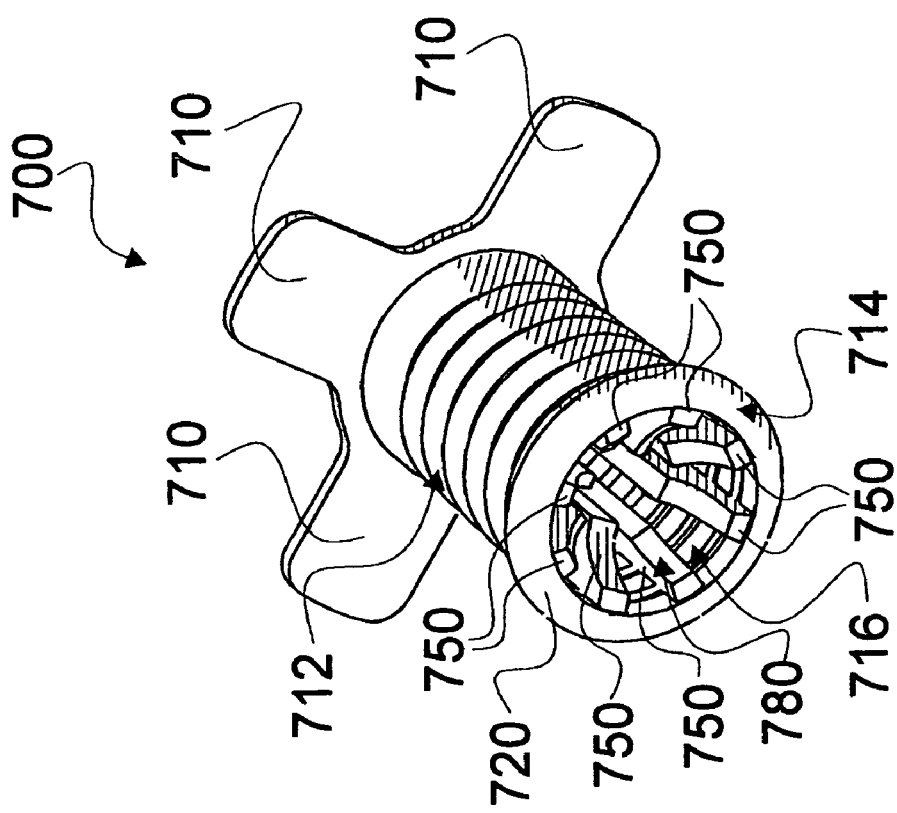
FIG. 11 is a perspective of a gas separator assembly disposed such that the rear of distal end is seen.
Figure 14:
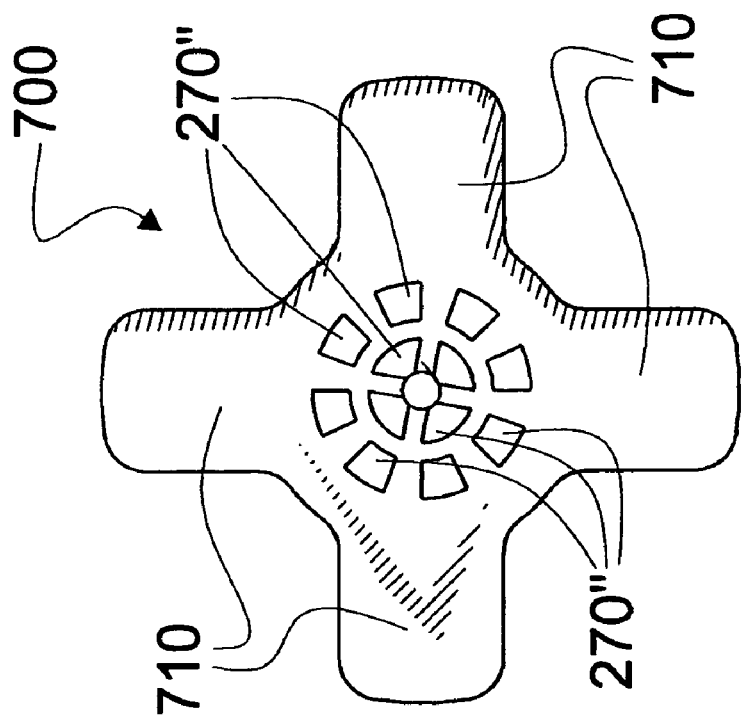
FIG. 14 is a front elevation of the gas separator assembly seen in FIG. 13.
Figure 13:
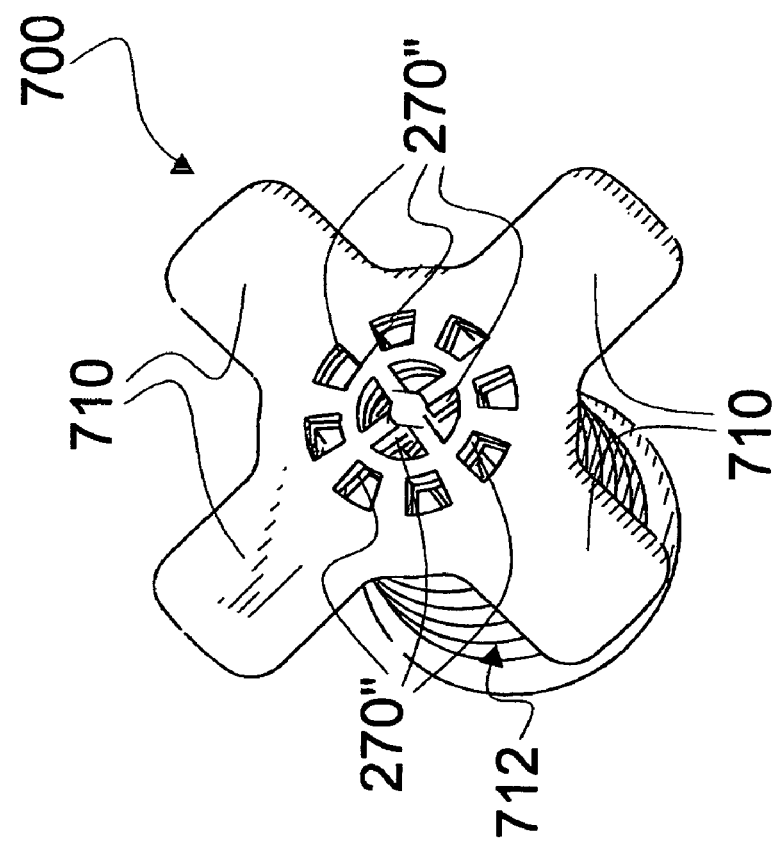
FIG. 13 is a perspective of the gas separator assembly seen in FIG. 11, but rotated such that the front or proximal end is seen.

As may be best seen in FIG. 11 body 712 comprises a plurality of medially directed ribs, generally numbered 750. Each distal surface 752 of each rib 750 comprises a curvature which is similar in size and radius of curvature of exterior surface 660 (see FIG. 10). However, in combination, surfaces 752 each have a sufficiently smaller radius of curvature 754 (see FIG. 15) than radius of curvature 660 to act as a clinch against proximal surface 624 of domed valve 610. Thus, in combination ribs 750 form a clinch 780 (see FIG. 15) which acts to maintain slit 680 (see FIG. 10) in a closed state when separator 700 is affixed to valved stopper 640 and a ΔP across dome valve 640 is negative.

Figure 17:
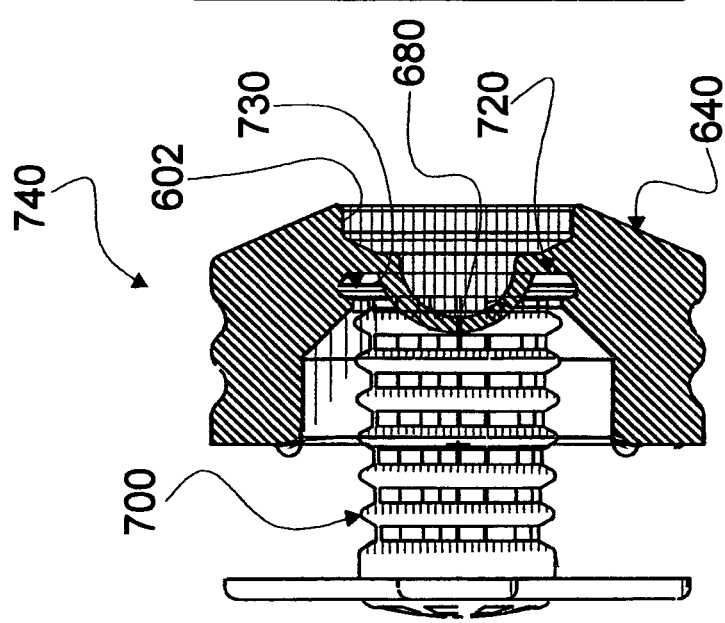
FIG. 17 is a side view of the valve assembly seen in FIG. 16 with a valve portion of the valved stopper seen in a first bi-stable or closed state.

A Valve Assembly Valve assembly 740 may be seen in various dispositions in FIGS. 16–18 with separator 700 securely affixed to valved stopper 640. In FIG. 17, separator 700 is shown as transparent, permitting dome valve 640 to be clearly seen. In FIG. 16, valve assembly 740 is disposed proximally apart from surface 554 such that slit 680 (see FIG. 17) remains closed keeping fluids residing in chambers 60 and 70 disparate. In FIG. 18, valve assembly 740 is disposed against a stop provided by surface 554 with sufficient force being exerted upon an associated plunger to create a sufficiently large positive ΔP to invert dome valve 640 and open slit 680. Note that indentation of dome valve 640 a distance defined by the width of wall 602 (see FIGS.

8 and 18), permits valve 640 to bulge outward upon opening without conflicting with surface 554.

Figure 19:
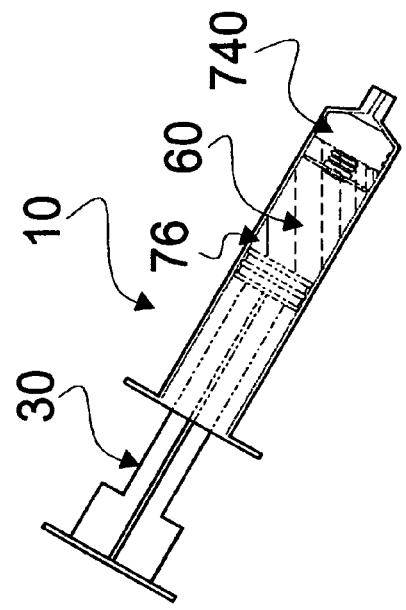
FIG. 19 is a side schematic view of a multi-chamber syringe fabricated according to the instant invention disclosed wherein is seen a valve assembly separating a filled proximal chamber from an empty distal chamber.
Figure 19A:
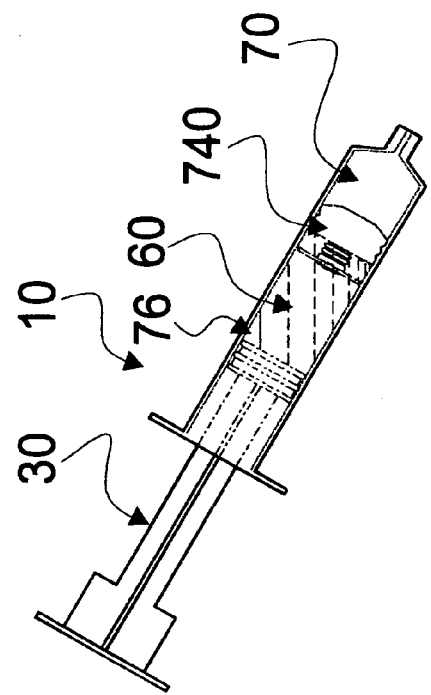
FIG. 19A is a side schematic view of the multi-chamber syringe seen in FIG. 19 with the valve assembly disposed in contact with an distal inner surface of a conventional syringe.
Figure 19B:
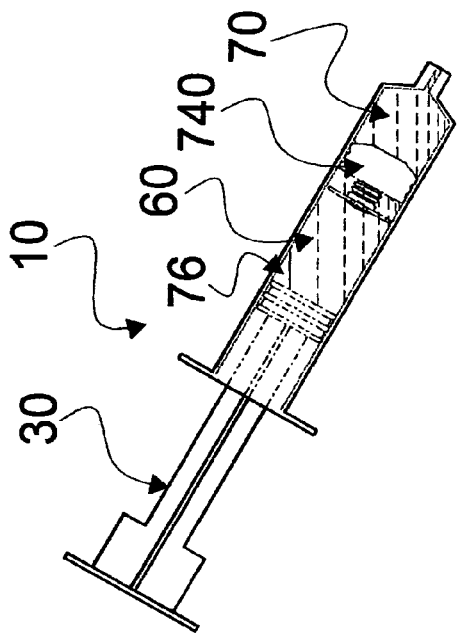
FIG. 19B is a side schematic view of the multi-chamber syringe seen in FIGS. 19 and 20 with liquid disposed in the distal chamber of the syringe.

Various modes of use of valve assembly 740 in a syringe 10 are seen in FIGS. 19, 19A–B, 20 and 20A–B. As seen in FIG. 19, valve assembly 740 is disposed to divide syringe 10 into two disparate chambers 60 and 70. A fluid comprising mostly liquid is disposed in chamber 60 while chamber 70 is empty. In FIG. 19A, a plunger 30 is displaced distally to likewise displace valve assembly 740 to empty chamber 70. Note that valve 640 (see in FIG. 17) remains closed as tactile and visual senses permit valve assembly 740 to be displaced to completely empty chamber 70 without activating (opening) valve 640. In FIG. 19B, plunger 30 is displaced proximally to withdraw liquid 790 into chamber 70, just as might be done with a conventional syringe without a valve assembly 740.

Figure 20A:
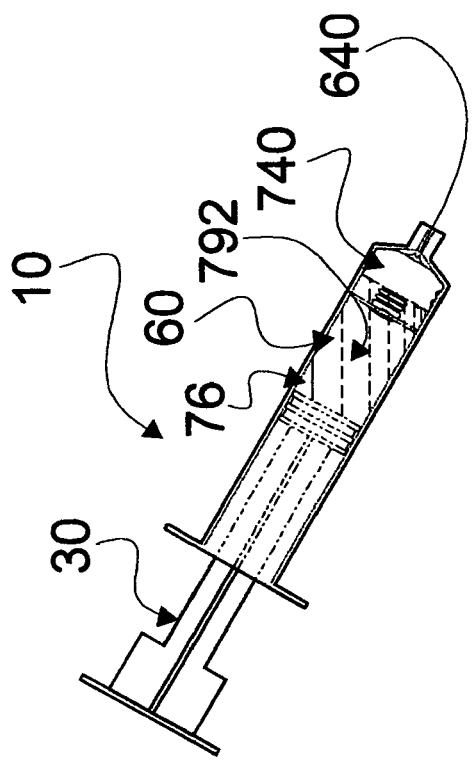
FIG. 20A is a side schematic view of the multi-chamber syringe seen in FIG. 20 with a valve of the valved assembly disposed in an open state.
Figure 20B:
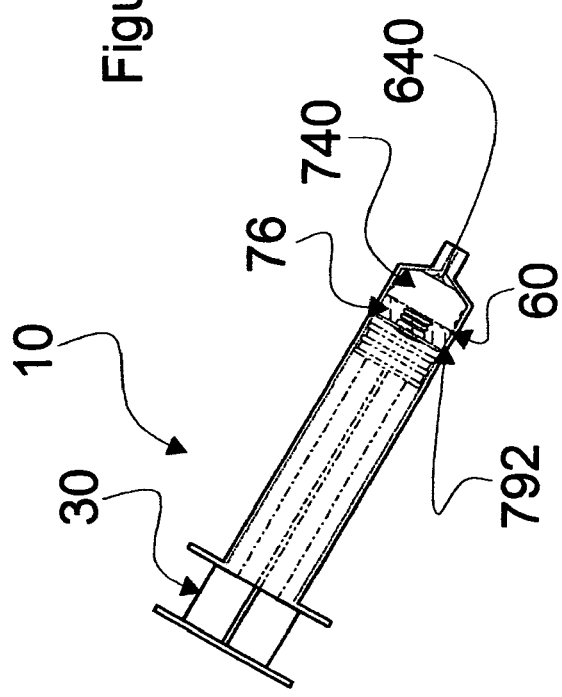
FIG. 20B is a side schematic view of the multi-chamber syringe seen in FIG. 20 with a valve of the valved assembly disposed in an open state and liquid dispensed from the proximal chamber.
Figure 20:
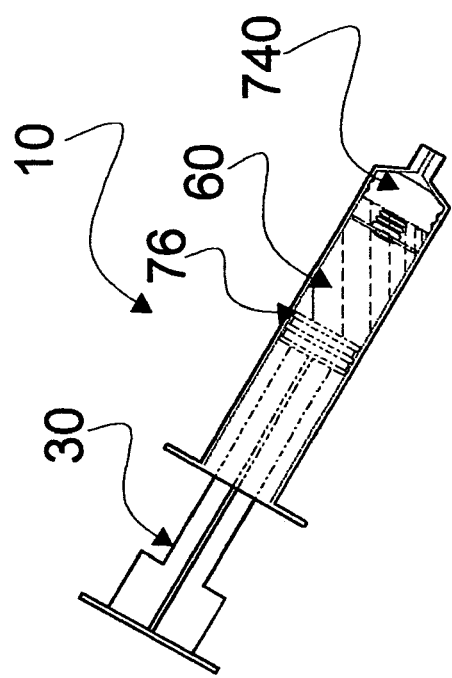
FIG. 20 is a side schematic view of the multi-chamber syringe seen in FIG. 19B with the valve assembly disposed against the distal inner surface of the syringe.

As seen in FIG. 20, plunger 30 has been displaced to cause valve assembly 740 to dispense liquid 790 from chamber 70 (see FIG. 19, as chamber 70 is totally evacuated in FIGS. 20 and 20A–B). However, note that a small residual of liquid 790 still resides in orifice 44. Flushing of such liquid 790 from orifice 44 and other spaces within a patient delivery system is one significant reason for using a multichamber syringe. Further an additional force disposed upon plunger 30 effectuates opening of valve 640 as seen in FIG. 20A.

Figure 25:
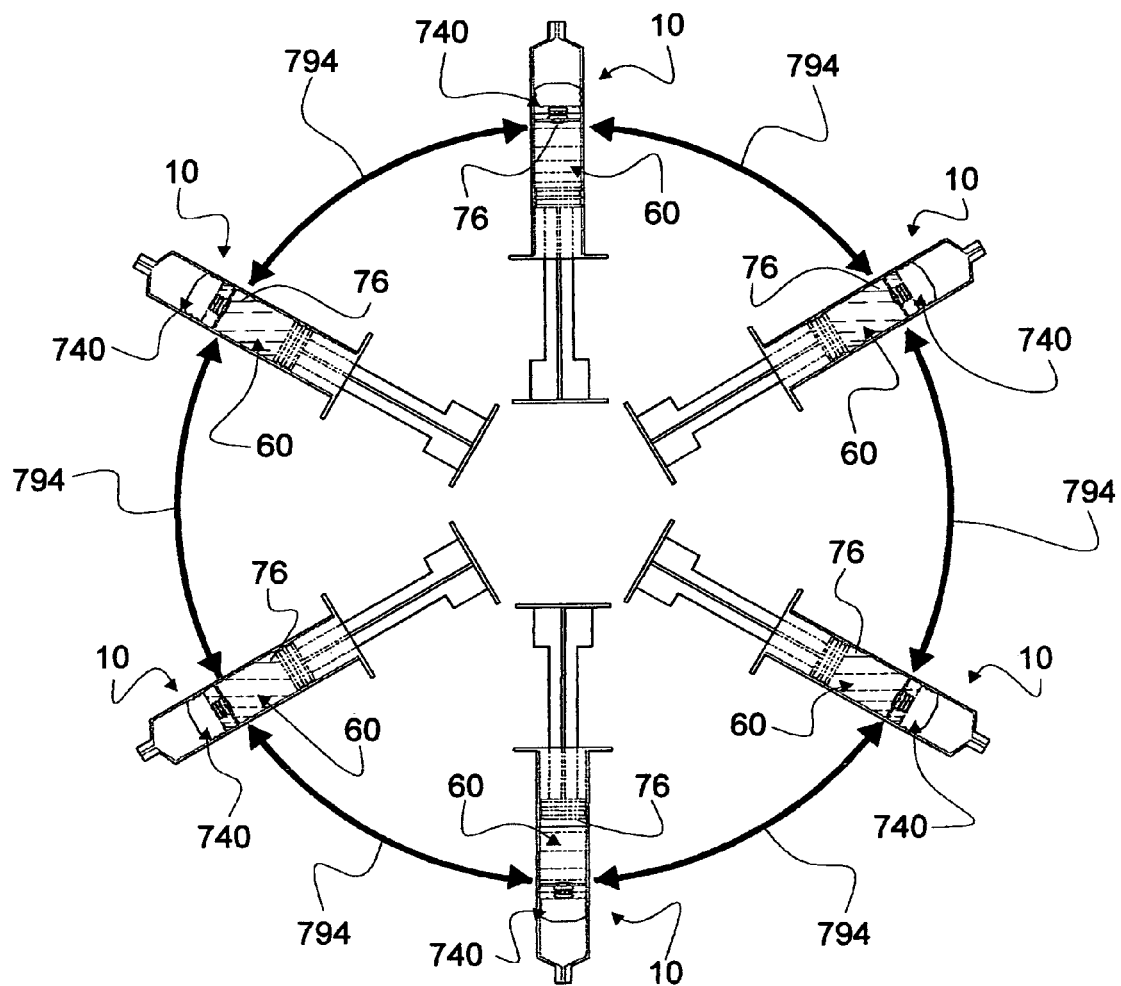
FIG. 25 is a schematic showing a plurality of syringes oriented in a plurality of multi-chamber syringes demonstrating multi-chamber syringes made in accordance with the instant invention may be used in any position relative to gravitational pull.

Continued application of distally directed force upon plunger 30 dispenses a large measure of the liquid content 792 of chamber 60. Note that any gas 76 (see FIGS. 2A and 20B) which was originally disposed in chamber 60, remains in chamber 60 and is not dispensed but remains with an undelivered portion of liquid 792. As seen in FIG. 25, a syringe 10 with a valve assembly 740 may be dispensed per the arrows, generally numbered 794 seen in FIGS. 19, 19A–B, 20 and 20A–B in any orientation relative to gravitational attraction without dispensing undesirable portions of gas 76 from chamber 60.

Figure 21:
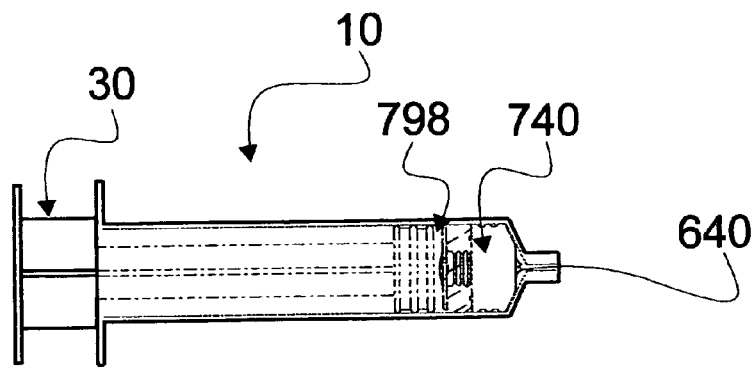
FIG. 21 is a lateral schematic view of the syringe seen in FIG. 20B.
Figure 22:
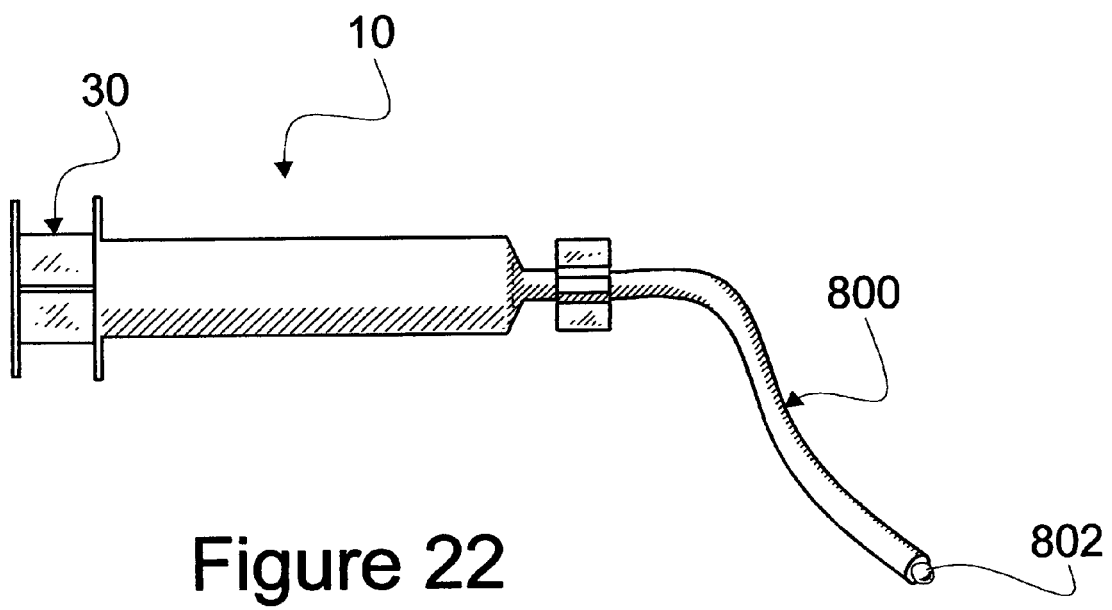
FIG. 22 is a lateral schematic view of the syringe seen in FIG. 21 with a tube attached and a drop of liquid being emitted from a distal end of the tube.

Reflux-free Operation A magnified and rotated view of syringe 10 and contents seen in FIG. 20B is seen in FIG. 21. It is important to note that plunger 30 has a catch 796 which inhibits plunger 30 from contacting valve assembly 740, thereby leaving a fluid buffer 798 disposed between plunger 30 and valve assembly 740. Due to contents of elastic material (e.g. gas or a rubber stopper of plunger 30) and due to valve 640 remaining in a bi-stable state whenever plunger 30 stops, a small positive flow continues to be dispensed from syringe 10. There is no negative flow allowed due to memory of the elastic material. For this reason, rather than reflux flow into a connected line 800, seen in FIG. 22, a small amount of liquid (seen as droplet 802) continues to be dispensed each time plunger 30 stops after valve 640 is open.

A Three Chamber Multi-chamber Syringe Set According to the Instant Invention On occasion it may be desirable to dispense a toxic medicine 810 from chamber 70 of a multi-chamber syringe made from a syringe 10 and valve assembly 740. In such a case, any contact through orifice 44 could be dangerous to a clinician or care giver. In such a situation, it would be preferable to provide an additional distal buffering capacity to provide an increased safety factor.

Figure 23:
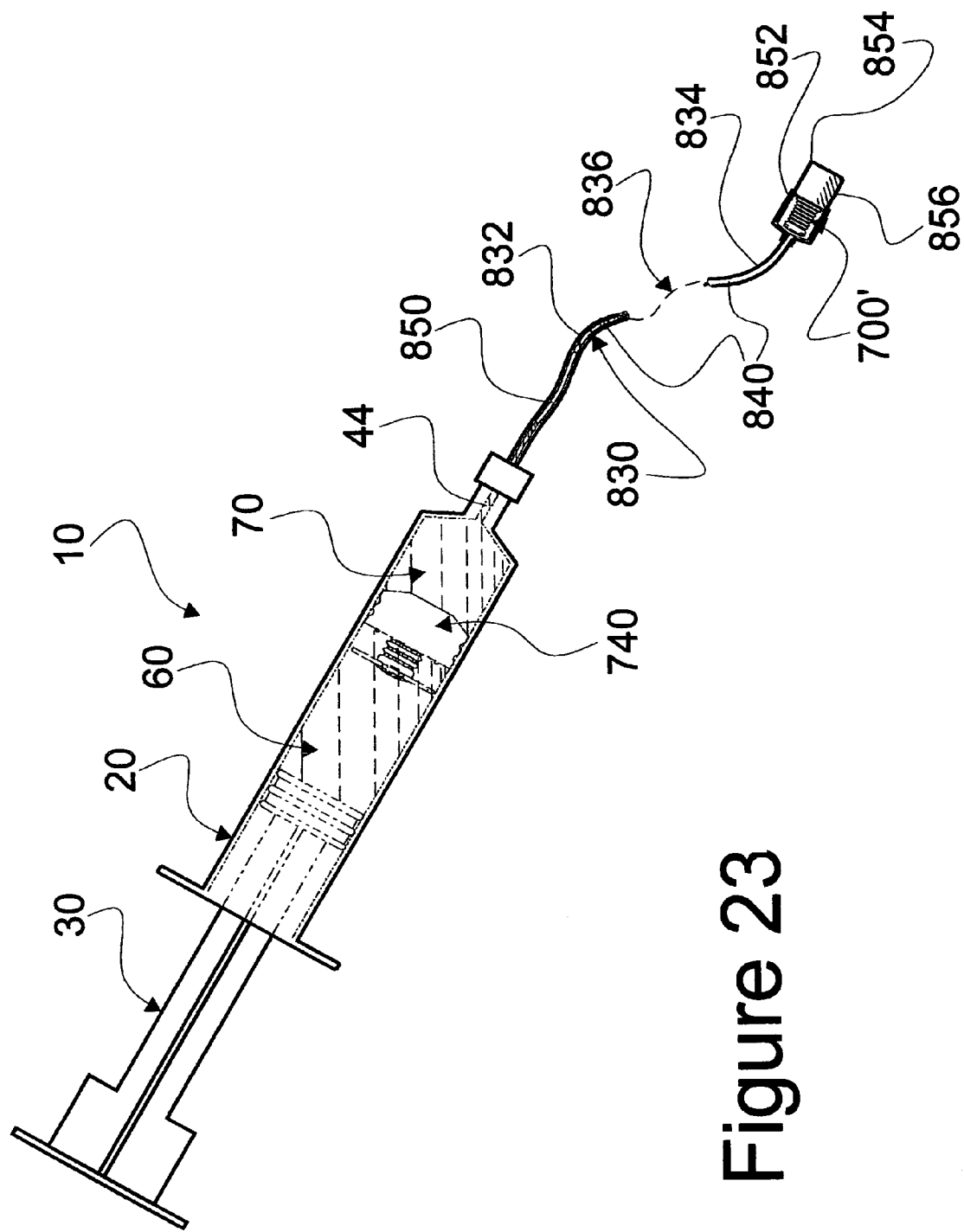
FIG. 23 is a side schematic of a multi-chamber syringe with an attached tubing set which contains an additional liquid chamber, liquid in the chamber being maintained disparate from liquid in the distal chamber by a gas bubble.
Figure 24:
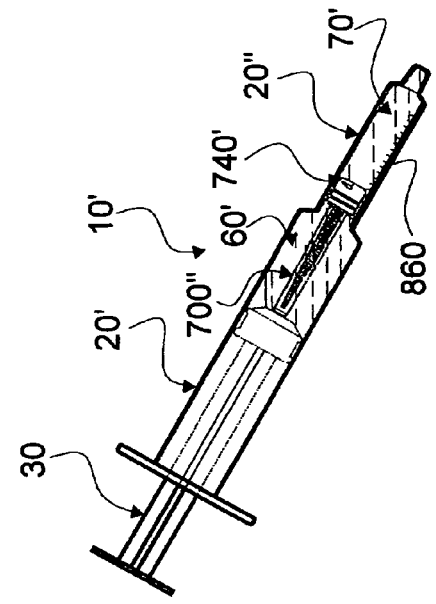
FIG. 24 is a side schematic of a multi-chamber syringe wherein an elongated barrel of the syringe comprises two sections, a proximal section being of larger diameter than the distal section, and a valve assembly disposed in the distal section to divide a proximal chamber from a distal chamber.
Figure 24A:
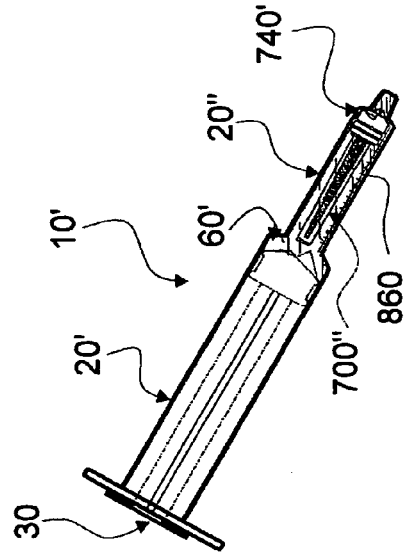
FIG. 24A is a side schematic of the multi-chamber syringe seen in FIG. 24 with liquid being disposed in each chamber.
Figure 24B:
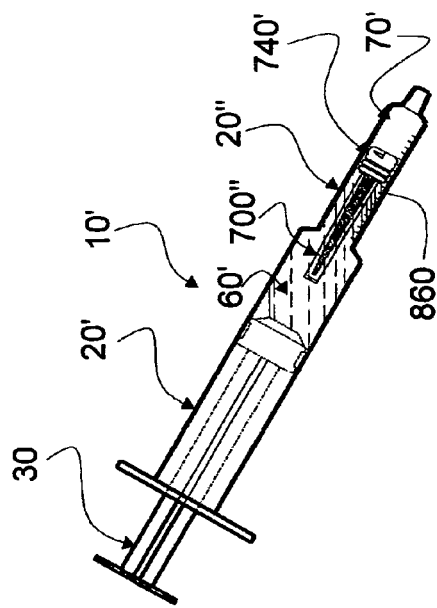
FIG. 24B is a side schematic of the multi-chamber syringe seen in FIG. 24 with liquid having been dispensed from the distal chamber.
Figure 24C:
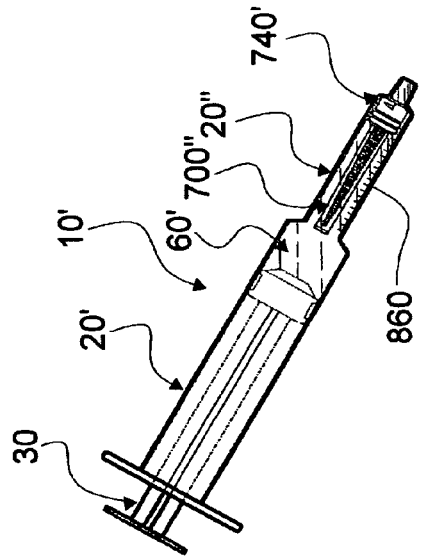
FIG. 24C is side schematic of the multi-chamber syringe seen in FIG. 24 with a valve of the valve assembly disposed in an open state and with liquid dispensed from the proximal chamber.

A combination 820 for such a purpose is seen in FIG. 23. Combination 820 includes a syringe 10 and a valve assembly 740 which divides barrel 20 into chambers 60 and 70. Syringe 10 is connected to a tubing set 830 comprising an elongated tubing shown in two parts 832 and 834 connected by a dashed line 836 for clarity of presentation. A buffer solution 840 which is hazard free is disposed within tubing set 830 such that any initial fluid dispensed from combination 820 will not be dangerous. To keep contents of chamber 60 disparate from solution 840, a gas (air) bubble 850 is disposed in a proximal portion of tubing set 830. It is well known in fluid processing art that such an air bubble will keep liquid, on opposite sides of the air bubble, disparate, thereby maintaining integrity of contents of chamber 70. Of course, gas (air) should not be dispensed from combination 820. For this reason an additional liquid filter 700' having similar filtering holes as those disclosed for separator 700 is provided in a chamber 852 disposed at a distal outlet portion 854 of tubing 834. Note also, that a preferable tubing connector 856, such as a luer fitting, is comprised within chamber 852 distal to filter 700'. In this manner, a multi-chamber syringe is increased in scope to a three chamber combination, with the third chamber being provided by tubing set 830.

A Precisely Fillable Multi-chamber Syringe In some applications of multi-chamber syringes, it is desirable to accurately fill a distal chamber, such as chamber 70, with a small volume liquid dose. Syringe barrels, such as barrel 20 may be too large to permit facilely derived, precision, small dose measurements. For this reason, a syringe, such as syringe 10', seen in FIGS. 24 and 24A–C, may be employed with a modified valve assembly 740'. Syringe 10' has a contiguous barrel which is divided into two sections, a proximal section 20' and a distal section 20". Proximal section 20' is easily seen to be larger in diameter than distal section 20". Valve assembly 740' comprises two parts, a valved stopper 640' and a separator 700". Note that a plunger 30 with an associated stopper is disposed and displaced within proximal section 20'. Valve assembly 740' is disposed distal section 20". Valve assembly divides syringe 10' into two chambers, proximal chamber 60' and distal chamber 70'. Of course, it is important that valve assembly 740' be perpetually retained in section 20".

It should be noted that, due to the relatively reduced diameter of section 20" relative to the diameter of section 20', for each unit of distance plunger 30 is displaced, valve assembly 740' is displaced a greater distance. To assure that valve assembly 740' is not extricated from section 20" by displacing plunger 30 too great a distance proximally, separator 700" is sufficiently elongated to contact a most distal portion of plunger 30 before valved stopper 640' is pulled from section 20". Because valve assembly 740' moves farther than plunger 30 in either direction, such contact effectively forms a lock which assures valve assembly 740' remains in section 20" (see FIG. 20A). Separator 700" comprises liquid filtering holes and features which affix separator 700" to valved stopper 640' in a manner similar to holes and features of separator 700 is affixed to valved stopper 640.

Note that a set of finely placed indicia 860 are imprinted upon a side of section 20" to facilitate precise measurement of liquid withdrawn into section 20". Dispensing of liquid from syringe 10' using valve assembly 740' is the same as dispensing liquid from syringe 10 using valve assembly 740. As may be noted in FIG. 24B, plunger 30 is displaced to force valve assembly 740' to be stopped at the distal end of syringe 10'. When thereat, additional force opens a slit valve of valved stopper 640' and liquid is dispensed therethrough.

This invention may be embodied in other specific forms without departing from the spirit or essential characteristics thereof. The present embodiments are therefore to be considered in all respects as illustrative and not restrictive, the scope of this invention being indicated by the appended claims rather than by the foregoing description, and all changes which come within the meaning and range of equivalency of the claims are therefore intended to be embraced therein.

What is claimed is:

1. A multi-chamber syringe apparatus for sequentially dispensing medical fluids, said apparatus comprising:
   a syringe barrel having an internal surface which is concentrically disposed about an elongated medial axis, said barrel surface comprising an open proximal end and a distal end having a closed interior about an orifice through which fluid is transferred;
   a stem and plunger combination disposed to be displaced within said barrel by application of a directional force against said stem for dislocating fluid thereby; and
   a valve assembly which, when disposed within said barrel between said plunger stopper and said distal end, provides a proximal chamber between the valve assembly and plunger stopper and a distal chamber between the valve assembly and said closed interior surface;
   said valve assembly comprising:
      a valved stopper comprising a normally closed, medially disposed valve in a distal face of the stopper and a hollow, grooved, cylindrical interior which opens proximally toward said plunger and which communicates with said plunger stopper via fluid, within the barrel, said valved stopper being distally displaced toward said distal end within said barrel when acted upon by a force directionally applied toward said distal end which produces a first differential pressure and being proximally displaced away from said distal end when acted upon by an oppositely directed force of a second differential pressure; and
      said valved stopper further comprising structure which only opens said valve to permit fluid flow there through when said stopper is acted upon by force of a third differential pressure which is in the same direction as force from the first differential pressure, the magnitude of the third differential pressure being greater than the first differential pressure.

2. A multi-chamber syringe apparatus according to claim 1 wherein said valved stopper comprises a bi-stable valve.

3. A multi-chamber syringe apparatus according to claim 1 comprises a slit valve comprising a medially disposed slit valve.

4. A multi-chamber syringe apparatus according to claim 3 wherein said bi-stable valve comprises a non-planar structure.

5. A multi-chamber syringe apparatus according to claim 4 wherein said non-planar valve comprises structure which defines operation of said valve to be bi-stable such that, once opened, said valve remains open.

6. A multi-chamber syringe apparatus according to claim 5 wherein said valved stopper further comprises a hinge disposed about said valve structure which articulates about said valve structure to permit the valve to be displaced to an open state when acted upon by force of said third differential pressure and to retain the valve in the open state, once opened.

7. A multi-chamber syringe apparatus according to claim 5 wherein said non-planar valve structure comprises a hemispherical dome shape.

8. A multi-chamber syringe apparatus according to claim 7 wherein said valved stopper further comprises a proximally disposed annular groove disposed to communicate through a wide proximal opening.

9. A multi-chamber syringe apparatus according to claim 1 wherein said valved stopper comprises material from which a syringe stopper is made.

10. A multi-chamber syringe apparatus according to claim 1 wherein said valved stopper comprises a distal frustoconical surface which substantially conforms to shape and size of a distal interior face of said syringe.

11. A multi-chamber syringe apparatus according to claim 8 wherein said valve assembly further comprises a separator which comprises a hollow-cylindrical body having a sealingly connecting structure, said structure comprising a shape and size relative to said stopper annular groove to permit said structure to be inserted into said annular groove to securely affix said separator to said stopper.

12. A multi-chamber syringe apparatus according to claim 11 wherein said structure and said each groove comprise a circular shape whereby said structure can be inserted into said groove in any radial orientation relative to said stopper.

13. A multi-chamber syringe apparatus according to claim 11 wherein said separator body comprises structure which is substantially closed at one end and has an open distal end, said open end being disposed about said slit when said connecting structure is disposed in contact with said annular groove.

14. A multi-chamber syringe apparatus according to claim 13 wherein said cylindrical body comprises a frustoconical shape.

15. A multi-chamber syringe apparatus according to claim 13 wherein said body comprises an outside surface and an inside surface and a plurality of holes displaced through the surfaces, said holes being sized and shaped to be permissive to liquid flow, but to impede gas flow to thereby act as a liquid filter which filters gas from liquid as liquid passes through the holes.

16. A multi-chamber syringe apparatus according to claim 11 wherein said cylindrical body comprises a plurality of internally directed elongated ribs which are radially displaced from said inside surface toward a hollow core of said body, said ribs comprising a clinching interface with said non-planar valve to, thereby, maintain said valve closed when force of the second differential pressure is imposed on the valve assembly.

17. A multi-chamber syringe apparatus according to claim 11 wherein said body comprises at least one hole disposed in a proximal side wherethrough gas is purged from the body.

18. A multi-chamber syringe apparatus according to claim 1 wherein the valve comprises a structure which requires a force which produces the third differential pressure to be tactilely discernable from the force which produces the first differential pressure.

19. A multi-chamber syringe apparatus according to claim 2 wherein said syringe comprises compressible matter within said proximal chamber such that, once said bi-stable valve is opened and, as a consequence of force applied to the stem to dispense liquid, energy is stored in said compressible matter which, once the force is removed from said stem, expanding decompression of said compressible matter inhibits reflux in an attached fluid line.

20. A multi-chamber syringe apparatus according to claim 11 wherein said apparatus further comprises a tubing set which effectively adds an additional chamber of liquid to said apparatus, said tubing set comprising:
   an elongated length of tubing comprising a proximal and a distal end and an elongated orifice therethrough;

a proximal connection at said proximal end whereby said tubing set is securely affixed to said distal end of said syringe barrel;

a volume of liquid disposed within said elongated orifice;

a bubble of gas disposed between said proximal connector and said volume of liquid;

a connector assembly disposed at the distal end of the tubing;

said connector assembly comprising a second liquid filter for filtering gas of said gas bubble from liquid delivered through the tubing.

21. A multi-chamber syringe apparatus according to claim 11 wherein said separator comprises stabilizing wings which extend outward from said body to contact said interior surface to thereby stabilize said valve assembly within said barrel.

22. A multi-chamber syringe apparatus according to claim 1 wherein said barrel comprises a proximal section having a substantially constant inside diameter and a distal section also having a substantially constant inside diameter, however said proximal section having a larger diameter than said distal section and wherein a plunger is disposed within said proximal section and a valve assembly is disposed within said distal section.

23. A method for using a multi-chamber syringe apparatus comprising the steps of:

providing said apparatus comprising:

a syringe barrel having an internal surface which is concentrically disposed about an elongated medial axis, said barrel surface comprising an open proximal end and a distal end having a closed interior about an orifice through which fluid is transferred;

a stem and plunger combination disposed to be displaced within said barrel by application of a directional force against said stem for dislocating fluid thereby; and a valve assembly disposed within said barrel between said plunger stopper and said distal end to provide a proximal chamber between the valve assembly and plunger stopper and a distal chamber between the valve assembly and said closed interior surface;

said valve assembly comprising:

a valved stopper comprising a normally closed, medially disposed valve in a distal face of the stopper and a hollow, grooved, cylindrical interior which opens proximally toward said plunger and which communicates with said plunger stopper via fluid, within the barrel, said valved stopper being distally displaced toward said distal end within said barrel when acted upon by a force directionally applied toward said distal end which produces a first differential pressure and being proximally displaced away from said distal end when acted upon by an oppositely directed force of a second differential pressure; and said valved stopper further comprising structure which opens said valve to permit fluid flow there through when said stopper is acted upon by force of a third differential pressure which is in the same direction as force from the first pressure, the magnitude of the third differential pressure being greater than the first differential pressure.

24. A method for using a multi-chamber syringe apparatus according to claim 23 comprising an additional step of filling said proximal chamber with a first fluid.

25. A method for using a multi-chamber syringe apparatus according to claim 24 comprising additional steps of filling and emptying a second fluid, respectively to and from said distal chamber, by displacing said stem and plunger in a conventional manner, while retaining the first fluid disparate from the second fluid.

26. A method for using a multi-chamber syringe apparatus according to claim 24 comprising a step of filling the distal chamber with a second fluid.

27. A method for using a multi-chamber syringe apparatus according to claim 26 comprising a step of clearing air from the distal chamber by conventional purging techniques, while maintaining the second fluid disparate from the first fluid.

28. A method for using a multi-chamber syringe apparatus according to claim 24 comprising an additional step of displacing said valve assembly, by force of said first differential pressure, to abut said distal end of said internal surface, thereby dispensing only the second fluid from said distal chamber.

29. A method for using a multi-chamber syringe apparatus according to claim 28 comprising an additional step of applying the force upon the stem to produce a third differential pressure which changes the valve from a closed stable state to an open stable state.

30. A method for using a multi-chamber syringe apparatus according to claim 29 comprising dispensing the first fluid from the syringe apparatus.

31. A method for using a multi-chamber syringe apparatus according to claim 24 wherein said filling step comprises filling said proximal chamber with a fluid, the major portion of which is a liquid, the rest being gas.

32. A method for using a multi-chamber syringe apparatus according to claim 31 wherein said first fluid dispensing step comprises filtering the fluid being dispensed from the chamber such that gas flow is impeded.

33. A valve assembly which, when disposed within a barrel of a syringe divides a predetermined portion of the barrel into a first chamber proximal to the valve assembly and a second chamber distal to the valve assembly, said valve assembly comprising:

a valved stopper comprising a normally closed, medially disposed valve in a distal face of the stopper and a hollow, grooved, cylindrical interior which opens proximally within said barrel and which communicates with pressure of fluid within the first and second chambers to be distally displaced within said barrel when acted upon by a first differential pressure and to be proximally displaced when acted upon by an oppositely directed differential force of a second differential pressure; and said valved stopper further comprising structure which only opens said valve to permit fluid flow there through when said stopper is acted upon by force of a third differential pressure which is in the same direction as force of the first differential pressure, the magnitude of the third differential pressure being greater than the first differential pressure.

34. A valve assembly according to claim 33 wherein said valved stopper comprises a bi-stable valve.

35. A valve assembly according to claim 34 comprises a slit valve comprising a medially disposed slit valve.

36. A valve assembly according to claim 35 wherein said bi-stable valve comprises a non-planar structure.

37. A valve assembly according to claim 36 wherein said non-planar valve comprises structure which defines operation of said valve to be bi-stable such that, once opened, said valve remains open.

38. A valve assembly according to claim 37 wherein said valved stopper further comprises a hinge disposed about said valve structure which articulates about said valve structure to permit the valve to be displaced to an open state when acted upon by force of said third differential pressure and to retain the valve in the open state, once opened.

39. A valve assembly according to claim 36 wherein said non-planar valve structure comprises a hemispherical dome shape.

40. A valve assembly according to claim 33 wherein said valved stopper further comprises a proximally disposed annular groove disposed to communicate through a wide proximal opening.

41. A valve assembly according to claim 33 wherein said valved stopper comprises material from which a syringe stopper is made.

42. A valve assembly according to claim 33 wherein said valved stopper comprises a distal frustoconical surface which substantially conforms to shape and size of a distal interior face of a syringe barrel.

43. A valve assembly according to claim 40 wherein said valve assembly further comprises a separator which comprises a hollow-cylindrical body having a sealingly connecting structure, said structure comprising a shape and size relative to said stopper annular groove to permit said structure to be inserted into said annular groove to securely affix said separator to said stopper.

44. A valve assembly according to claim 43 wherein said structure and said each groove comprise a circular shape whereby said structure can be inserted into said groove in any radial orientation relative to said stopper.

45. A valve assembly according to claim 11 wherein said separator body comprises structure which is substantially closed at one end and has an open distal end, said open end being disposed about said slit when said connecting structure is disposed in contact with said annular groove and said substantially closed end comprising at least one hole.

46. A valve assembly according to claim 43 wherein said hollow-cylindrical body comprises a frustoconical shape.

47. A valve assembly according to claim 43 wherein said hollow-cylindrical body comprises an outside surface and an inside surface and a plurality of holes displaced through the surfaces, said holes being sized and shaped to be permissive to liquid flow, but to impede gas flow to thereby act as a liquid filter which filters gas from liquid as liquid passes through the holes.

48. A valve assembly according to claim 43 wherein said hollow-cylindrical body comprises a plurality of internally directed elongated ribs which are radially displaced from said inside surface toward a hollow core of said body, said ribs comprising a clinching interface with said non-planar valve to, thereby, maintain said valve closed when force of the second differential pressure is imposed on the valve assembly.

49. A valve assembly according to claim 45 wherein said body comprises at least one hole disposed in a proximal side wherethrough gas is purged from the body.

50. A valve assembly according to claim 33 wherein the valved stopper comprises a structure which requires a force producing the third differential pressure to be tactilely discernable from a force producing the first differential pressure.

51. A valve assembly according to claim 43 wherein said separator comprises stabilizing wings which extend outward from said body to contact an interior surface of a syringe barrel in which said valve assembly is disposed to thereby stabilize said valve assembly within the barrel.

52. A tubing set for adding a chamber of liquid to a dispensing vessel containing a fluid to be dispensed therefrom, said tubing set comprising:

an elongated length of tubing comprising a proximal and a distal end and an elongated orifice therethrough;

a proximal connection at said proximal end whereby said tubing set is securely affixed to the dispensing vessel;

a volume of liquid disposed within said elongated orifice;

a bubble of gas separating said proximal end from said volume of liquid to thereby make the fluid in the dispensing vessel disparate from said volume of liquid;

a connector assembly disposed at the distal end of the tubing;

said connector assembly comprising a liquid filter gas separator whereby gas of said gas bubble is filtered from liquid delivered through the tubing.

* * * * *